United States Patent
Kim et al.

(10) Patent No.: US 12,108,667 B2
(45) Date of Patent: Oct. 1, 2024

(54) ORGANIC ELECTROLUMINESCENCE DEVICE AND SPIRO COMPOUND FOR ORGANIC ELECTROLUMINESCENCE DEVICE

(71) Applicant: Samsung Display Co., Ltd., Yongin-si (KR)

(72) Inventors: Seulong Kim, Hwaseong-si (KR); Kyungsik Kim, Suwon-si (KR); Sungwook Kim, Hwaseong-si (KR); Sung-Soo Bae, Seoul (KR); Jaeweon Hur, Busan (KR)

(73) Assignee: Samsung Display Co., Ltd., Yongin-si (KR)

( * ) Notice: Subject to any disclaimer, the term of this patent is extended or adjusted under 35 U.S.C. 154(b) by 726 days.

(21) Appl. No.: 17/293,309

(22) PCT Filed: Apr. 15, 2019

(86) PCT No.: PCT/KR2019/004532
§ 371 (c)(1),
(2) Date: May 12, 2021

(87) PCT Pub. No.: WO2020/122327
PCT Pub. Date: Jun. 18, 2020

(65) Prior Publication Data
US 2021/0408397 A1    Dec. 30, 2021

(30) Foreign Application Priority Data
Dec. 14, 2018 (KR) .................. 10-2018-0162223

(51) Int. Cl.
*H01L 51/00* (2006.01)
*H10K 85/40* (2023.01)
*H10K 85/60* (2023.01)
*H10K 50/11* (2023.01)
*H10K 101/10* (2023.01)

(52) U.S. Cl.
CPC ......... *H10K 85/6572* (2023.02); *H10K 85/40* (2023.02); *H10K 85/615* (2023.02); *H10K 85/636* (2023.02); *H10K 85/654* (2023.02); *H10K 85/6574* (2023.02); *H10K 50/11* (2023.02); *H10K 2101/10* (2023.02)

(58) Field of Classification Search
CPC ............ H01L 51/0072; H01L 51/0061; H01L 51/0067; H01L 51/5016; H01L 51/0094; H01L 51/0052; H01L 51/0073
USPC ......................................................... 428/690
See application file for complete search history.

(56) References Cited

U.S. PATENT DOCUMENTS

| | | | |
|---|---|---|---|
| 9,985,216 B2 | 5/2018 | Nagaoka et al. | |
| 11,217,754 B2 | 1/2022 | Hodogaya | |
| 2016/0211454 A1 | 7/2016 | Kim et al. | |
| 2017/0179395 A1 | 6/2017 | Kim et al. | |

FOREIGN PATENT DOCUMENTS

| | | | |
|---|---|---|---|
| CN | 104557875 A | | 4/2015 |
| CN | 107078224 A | | 8/2017 |
| KR | 10-2015-0008678 A | | 1/2015 |
| KR | 10-2015-0069235 A | | 6/2015 |
| KR | 10-2015-0070928 A | | 6/2015 |
| KR | 20150144121 A | * | 6/2015 |
| KR | 10-2015-0111106 A | | 10/2015 |
| KR | 10-2016-0017055 A | | 2/2016 |
| KR | 10-1717988 B1 | | 3/2017 |
| KR | 10-2017-0075123 A | | 7/2017 |

OTHER PUBLICATIONS

Translation of DR 2015-0070928, Jun. 25, 2015. (Year: 2015).*
International Search Report for corresponding Application No. PCT/KR2019/004532 dated Sep. 9, 2019, 4 pp.

* cited by examiner

*Primary Examiner* — Hui H Chin
(74) *Attorney, Agent, or Firm* — Lewis Roca Rothgerber Christie LLP

(57) ABSTRACT

An organic electroluminescence device of an embodiment includes a first electrode, a hole transport region on the first electrode, an emission layer on the hole transport region, an electron transport region on the emission layer and a second electrode on the electron transport region, wherein the emission layer includes a spiro compound containing an aryl amine group and an indenoindole derivative, thereby showing high emission efficiency and the emission layer emits green light.

12 Claims, 2 Drawing Sheets

ORGANIC ELECTROLUMINESCENCE DEVICE AND SPIRO COMPOUND FOR ORGANIC ELECTROLUMINESCENCE DEVICE

CROSS-REFERENCE TO RELATED APPLICATIONS

This application is a U.S. National Phase Patent Application of International Patent Application Number PCT/KR2019/004532, filed on Apr. 15, 2019, which claims priority to Korean Patent Application Number 10-2018-0162223, filed on Dec. 14, 2018, the entire content of each of which is hereby incorporated by reference.

FIELD

The subject matter disclosed herein relates to an organic electroluminescence device and a spiro compound used therein.

BACKGROUND

Recently, the development of an organic electroluminescence display as an image display is being actively conducted. Different from a liquid crystal display, the organic electroluminescence display is so-called a self-luminescent display in which holes and electrons injected from a first electrode and a second electrode recombine in an emission layer so that a light-emitting material including an organic compound in the emission layer emits light to attain display.

In the application of an organic electroluminescence device to a display, the decrease of the driving voltage, and the increase of the emission efficiency and the life of the organic electroluminescence device are required, and development on materials for an organic electroluminescence device stably attaining the requirements is being continuously required.

Particularly, recently, in order to accomplish an organic electroluminescence device with high efficiency, technique on phosphorescence emission which uses energy in a triplet state or delayed fluorescence emission which uses the generating phenomenon of singlet excitons by the collision of triplet excitons (triplet-triplet annihilation, TTA) is being developed, and development on a material for thermally activated delayed fluorescence (TADF) using delayed fluorescence phenomenon is being conducted.

SUMMARY

An object of embodiments of the present disclosure is to provide an organic electroluminescence device having improved green emission efficiency.

Another object of embodiments of the present disclosure is to provide a spiro compound capable of improving emission efficiency.

An embodiment of the present disclosure provides an organic electroluminescence device including a first electrode, a hole transport region on the first electrode, an emission layer on the hole transport region, an electron transport region on the emission layer and a second electrode on the electron transport region, wherein the emission layer includes a spiro compound containing an aryl amine group and an indenoindole derivative and the emission layer emits green light.

In the spiro compound, the indenoindole derivative and a pentagonal or hexagonal ring of the spiro compound may form a spiro bond.

The indenoindole derivative and the aryl amine group may be bonded via a linker or via a direct linkage.

The emission layer may be a thermally activated delayed fluorescence emission layer.

The spiro compound may have an absolute value of a difference between a singlet energy level and a triplet energy level of 0.2 eV or less.

The emission layer may include a host and a dopant, and the dopant may include the spiro compound.

The spiro compound may be represented by Formula 1 below.

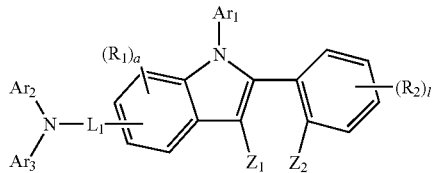

Formula 1

In Formula 1, $R_1$ and $R_2$ are each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, or combined with an adjacent group to form a ring, $Ar_1$ is a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, $Ar_2$ and $Ar_3$ are each independently a substituted or unsubstituted aryl group of 6 to 30 ring-forming carbon atoms, or a substituted or unsubstituted heteroaryl group of 2 to 30 ring-forming carbon atoms, $L_1$ is a direct linkage, a substituted or unsubstituted arylene group of 6 to 30 ring-forming carbon atoms, or a substituted or unsubstituted heteroarylene group of 2 to 30 ring-forming carbon atoms, a is an integer of 0 to 3, l is an integer of 0 to 4, and $Z_1$ and $Z_2$ form spiro bonds of a ring compound represented by Formula 2 below.

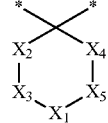

Formula 2

In Formula 2, $X_1$ is a direct linkage, O, S, $CR_5R_6$, $SiR_7R_8$, $BR_9$, or $NR_{10}$, $X_2$ to $X_5$ are each independently $CR_{11}R_{12}$, $R_5$ to $R_{12}$ are each independently a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, and * indicates a binding site to an adjacent atom of Formula 1.

Formula 2 may be represented by any one selected from among Formula 2-1 to Formula 2-7 below.

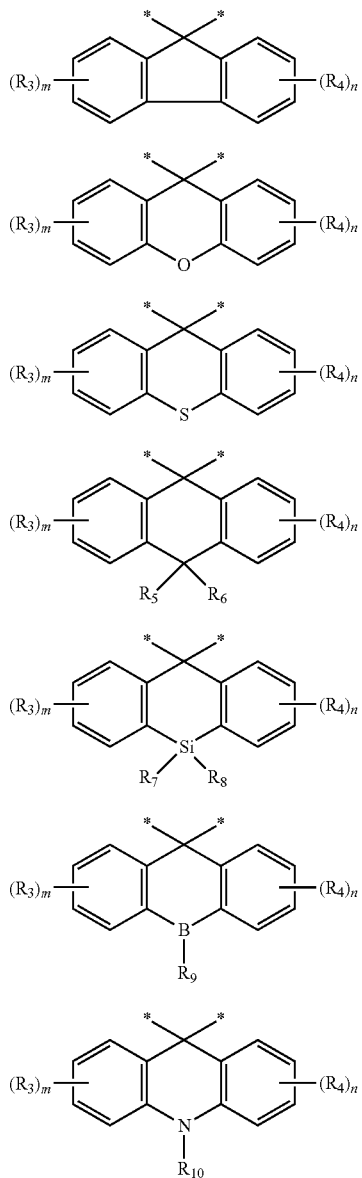

In Formula 2-1 to Formula 2-7, $R_3$ and $R_4$ are each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, or combined with an adjacent group to form a ring, m and n are each independently an integer of 0 to 4, $R_5$ to $R_{10}$ are the same as defined in Formula 2, and * indicates a binding site to an adjacent atom of Formula 1.

Formula 1 may be represented by Formula 3 below.

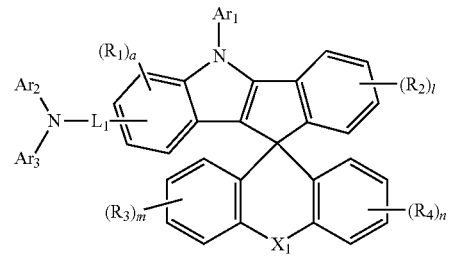

In Formula 3, $R_3$ and $R_4$ are each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, or combined with an adjacent group to form a ring, m and n are each independently an integer of 0 to 4, and $R_1$, $R_2$, $R_5$ to $R_{10}$, $Ar_1$ to $Ar_3$, $L_1$, $X_1$, a, and l are the same as defined in Formula 1 and Formula 2.

An embodiment of the present disclosure provides an organic electroluminescence device including a first electrode, a hole transport region on the first electrode, an emission layer on the hole transport region, an electron transport region on the emission layer, and a second electrode on the electron transport region, wherein the emission layer includes a spiro compound represented by Formula 1 below.

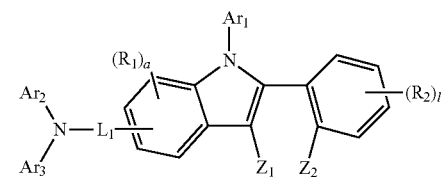

In Formula 1, $R_1$ and $R_2$ are each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, or combined with an adjacent group to form a ring, $Ar_1$ is a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, Ar$_2$ and Ar$_3$ are each independently a substituted or unsubstituted aryl group of 6 to 30 ring-forming carbon atoms, or a substituted or unsubstituted heteroaryl group of 2 to 30 ring-forming carbon atoms, L$_1$ is a direct linkage, a substituted or unsubstituted arylene group of 6 to 30 ring-forming carbon atoms, or a substituted or unsubstituted heteroarylene group of 2 to 30 ring-forming carbon atoms, a is an integer of 0 to 3, 1 is an integer of 0 to 4, and Z$_1$ and Z$_2$ form spiro bonds of a ring compound represented by Formula 2 below.

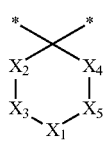

Formula 2

In Formula 2, X$_1$ is a direct linkage, O, S, CR$_5$R$_6$, SiR$_7$R$_8$, BR$_9$, or NR$_{10}$, X$_2$ to X$_5$ are each independently CR$_{11}$R$_{12}$, R$_5$ to R$_{12}$ are each independently a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, and * indicates a binding site to an adjacent atom of Formula 1.

The present disclosure provides a spiro compound represented by Formula 1 below.

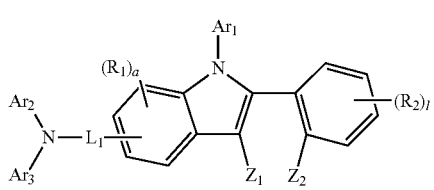

Formula 1

In Formula 1, R$_1$ and R$_2$ are each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, or combined with an adjacent group to form a ring, Ar$_1$ is a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, Ar$_2$ and Ar$_3$ are each independently a substituted or unsubstituted aryl group of 6 to 30 ring-forming carbon atoms, or a substituted or unsubstituted heteroaryl group of 2 to 30 ring-forming carbon atoms, L$_1$ is a direct linkage, a substituted or unsubstituted arylene group of 6 to 30 ring-forming carbon atoms, or a substituted or unsubstituted heteroarylene group of 2 to 30 ring-forming carbon atoms, a is an integer of 0 to 3, 1 is an integer of 0 to 4, and Z$_1$ and Z$_2$ form spiro bonds of a ring compound represented by Formula 2 below.

Formula 2

In Formula 2, X$_1$ is a direct linkage, O, S, CR$_5$R$_6$, SiR$_7$R$_8$, BR$_9$, or NR$_{10}$, X$_2$ to X$_5$ are each independently CR$_{11}$R$_{12}$, R$_5$ to R$_{12}$ are each independently a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, and * indicates a binding site to an adjacent atom of Formula 1.

The organic electroluminescence device according to an embodiment of the present disclosure may attain high efficiency and long life in a green emission region.

The spiro compound according to an embodiment of the present disclosure may improve the life and efficiency of an organic electroluminescence device.

DETAILED DESCRIPTION

Figure 1:
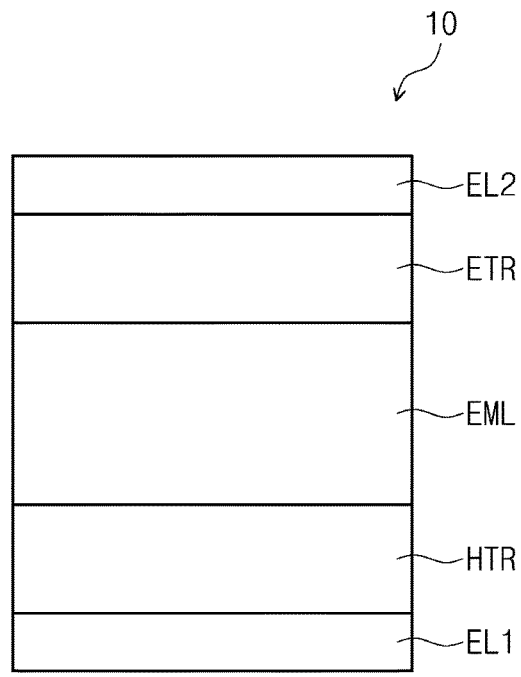
FIG. 1 is a cross-sectional view schematically showing an organic electroluminescence device according to an embodiment of the present disclosure.

The subject matter of the present disclosure may have various modifications and may be embodied in different forms, and example embodiments will be explained in more detail with reference to the accompany drawings. The subject matter of the present disclosure may, however, be embodied in different forms and should not be construed as limited to the embodiments set forth herein. Rather, the subject matter of the present disclosure should be considered to include all modifications, equivalents, and substituents which are included in the spirit and technical scope of the present disclosure.

Like reference numerals refer to like elements throughout. In addition, in the drawings, the dimensions of constituent elements may be exaggerated for effective explanation of technical contents. It will be understood that, although the terms first, second, etc. may be used herein to describe various elements, these elements should not be limited by these terms. These terms are only used to distinguish one element from another element. For example, a first element could be termed a second element without departing from the spirit and scope of the present disclosure. Similarly, a second element could be termed a first element. The singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combinations thereof, but do not preclude the presence or addition of one or more other features, numerals, steps, operations, elements, parts, or the combinations thereof. In addition, it will be understood that when a part including a layer, a film, a region, a plate, etc. is referred to as being "on" another part, it can be "directly on" another part or intervening third parts may be present.

Hereinafter, an organic electroluminescence device according to an embodiment of the present disclosure will be explained with reference to FIG. 1 to FIG. 3.

Figure 2:
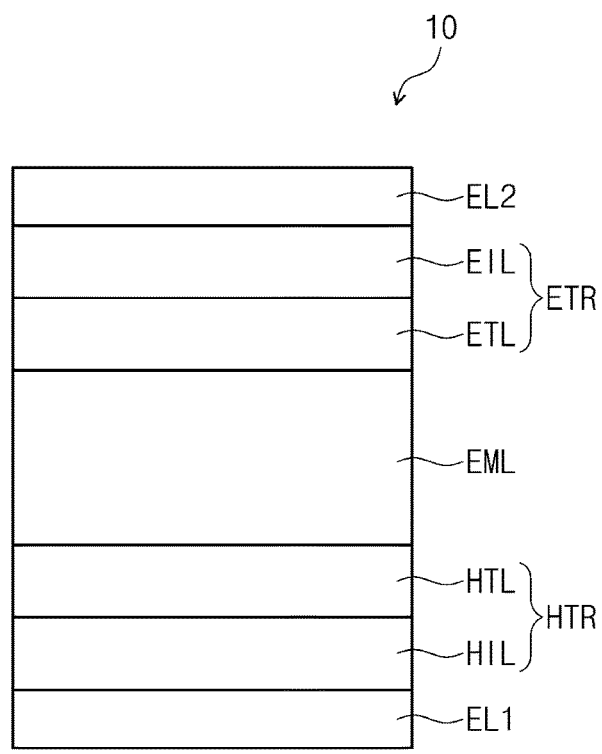
FIG. 2 is a cross-sectional view schematically showing an organic electroluminescence device according to an embodiment of the present disclosure.
Figure 3:
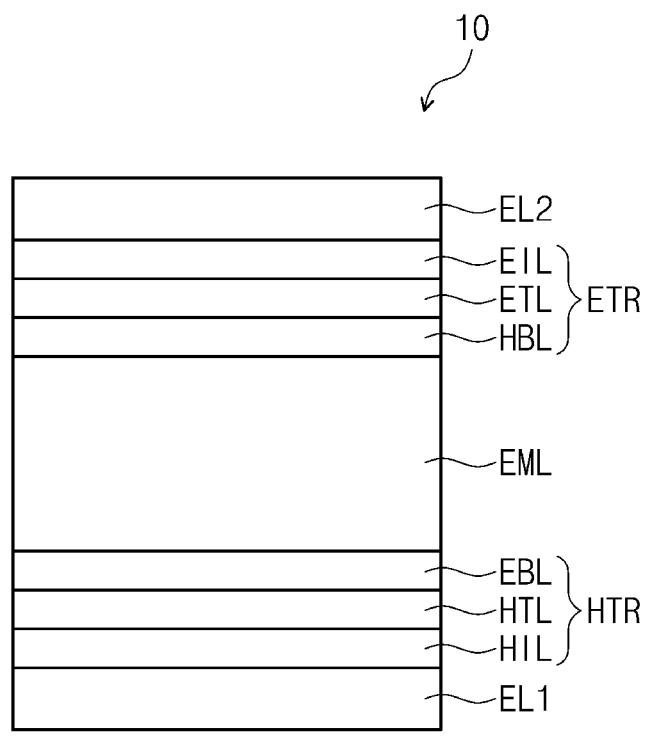
FIG. 3 is a cross-sectional view schematically showing an organic electroluminescence device according to an embodiment of the present disclosure.

Referring to FIG. 1 to FIG. 3, an organic electroluminescence device (10) according to an embodiment may include a first electrode (EL1), a hole transport region (HTR), an emission layer (EML), an electron transport region (ETR) and a second electrode (EL2), stacked in order.

The first electrode (EL1) and the second electrode (EL2) are oppositely disposed to each other, and between the first electrode (EL1) and the second electrode (EL2), multiple organic layers may be disposed. The multiple organic layers may include the hole transport region (HTR), the emission layer (EML), and the electron transport region (ETR). The organic electroluminescence device (10) of an embodiment may include the above-described spiro compound of an embodiment in the emission layer (EML).

Meanwhile, when compared with FIG. 1, FIG. 2 shows the cross-sectional view of an organic electroluminescence device (10) of an embodiment, wherein a hole transport region (HTR) includes a hole injection layer (HIL) and a hole transport layer (HTL), and an electron transport region (ETR) includes an electron injection layer (EIL) and an electron transport layer (ETL). In addition, when compared with FIG. 1, FIG. 3 shows the cross-sectional view of an organic electroluminescence device (10) of an embodiment, wherein a hole transport region (HTR) includes a hole injection layer (HIL), a hole transport layer (HTL), and an electron blocking layer (EBL), and an electron transport region (ETR) includes an electron injection layer (EIL), an electron transport layer (ETL), and a hole blocking layer (HBL).

The organic electroluminescence device (10) of one or more embodiments, shown in FIG. 1 to FIG. 3, may include the spiro compound of an embodiment in at least one organic layer among multiple organic layers.

In the organic electroluminescence device (10) of an embodiment, the first electrode (EL1) has conductivity. The first electrode (EL1) may be formed using a metal alloy or a conductive compound. The first electrode (EL1) may be an anode.

The first electrode (EL1) may be a transmissive electrode, a transflective electrode, or a reflective electrode. If the first electrode (EL1) is the transmissive electrode, the first electrode (EL1) may be formed using a transparent metal oxide, for example, indium tin oxide (ITO), indium zinc oxide (IZO), zinc oxide (ZnO), indium tin zinc oxide (ITZO), etc. If the first electrode (EL1) is the transflective electrode or the reflective electrode, the first electrode (EL1) may include Ag, Mg, Cu, Al, Pt, Pd, Au, Ni, Nd, Ir, Cr, Li, Ca, LiF/Ca, LiF/Al, Mo, Ti, compounds thereof, or mixtures thereof (for example, a mixture of Ag and Mg). Alternatively, a structure including a plurality of layers including a reflective layer or a transflective layer formed using the above materials, and a transmissive conductive layer formed using indium tin oxide (ITO), indium zinc oxide (IZO), zinc oxide (ZnO), indium tin zinc oxide (ITZO) etc., may be formed. For example, the first electrode (EL1) may include a multilayer structure of ITO/Ag/ITO.

The hole transport region (HTR) is provided on the first electrode (EL1). The hole transport region (HTR) may include at least one selected from among a hole injection layer (HIL), a hole transport layer (HTL), a hole buffer layer and an electron blocking layer (EBL).

The hole transport region (HTR) may have a single layer formed using a single material, a single layer formed using a plurality of different materials, or a multilayer structure including a plurality of layers formed using a plurality of different materials.

For example, the hole transport region (HTR) may have the structure of a single layer of a hole injection layer (HIL) or a hole transport layer (HTL), and may have a structure of a single layer formed using a hole injection material and a hole transport material. Alternatively, the hole transport region (HTR) may have a structure of a single layer formed using a plurality of different materials, or a structure stacked from the first electrode (EL1) of hole injection layer (HIL)/hole transport layer (HTL), hole injection layer (HIL)/hole transport layer (HTL)/hole buffer layer, hole injection layer (HIL)/hole buffer layer, hole transport layer (HTL)/hole buffer layer, or hole injection layer (HIL)/hole transport layer (HTL)/electron blocking layer (EBL), but embodiments are not limited thereto.

The hole transport region (HTR) may be formed using various suitable methods such as a vacuum deposition method, a spin coating method, a cast method, a Langmuir-Blodgett (LB) method, an inkjet printing method, a laser printing method, and/or a laser induced thermal imaging (LITI) method.

The hole injection layer (HIL) of the organic electroluminescence device (10) of an embodiment may include any suitable hole injection materials used in the art. For example, the hole injection layer (HIL) may include triphenylamine-containing polyetherketone (TPAPEK), 4-isopropyl-4'-methyldiphenyliodoniumtetrakis(pentafluorophenyl)borate (PPBI), N,N'-diphenyl-N,N'-bis-[4-(phenyl-m-tolyl-amino)-phenyl]-phenyl-4,4'-diamine (DNTPD), a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine (NPB), N,N'-bis(1-naphthyl)-N,N'-diphenyl-4,4'-diamine (α-NPD), 4,4',4''-tris{N,N diphenylamino}triphenylamine (TDATA), 4,4',4''-tris(N,N-2-naphthyl phenylamino)triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), and/or dipyrazino[2,3-f: 2',3'-h]quinoxaline-2,3,6,7,10,11-hexacarbonitrile (HAT-CN). However, embodiments are not limited thereto.

The hole transport layer (HTL) of the organic electroluminescence device (10) of an embodiment may include any suitable hole transport materials used in the art. For example, the hole transport layer (HTL) may include 1,1-bis[(di-4-tolylamino)phenyl]cyclohexane (TAPC), carbazole derivatives such as N-phenyl carbazole and polyvinyl carbazole, N,N'-bis(3-methylphenyl)-N,N'-diphenyl-[1,1-biphenyl]-4,4'-diamine (TPD), 4,4',4''-tris(N-carbazolyl)triphenylamine (TCTA), or N,N'-di(1-naphthyl)-N,N'-diphenylbenzidine (NPB), N,N'-bis(1-naphthyl)-N,N'-diphenyl-4,4'-diamine (α-NPD), etc. However, embodiments are not limited thereto.

Meanwhile, the hole transport region (HTR) may further include an electron blocking layer (EBL), and the electron blocking layer (EBL) may be between the hole transport layer (HTL) and the emission layer (EML). The electron blocking layer (EBL) may be a layer playing the role of preventing or reducing injection of electrons from the electron transport region (ETR) to the hole transport region (HTR).

The electron blocking layer (EBL) may include any suitable materials used in the art (e.g., any suitable material used for an electron blocking layer). The electron blocking layer (EBL) may include, for example, carbazole derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris(N-carbazolyl)triphenylamine (TCTA), N,N'-di(naphthalene-1-yl)-N,N'-diphenyl-benzidine (NPD), 4,4'-cyclohexylidene bis[N,N-bis(4-methylphenyl)benzenamine (TAPC), 4,4'-bis[N,N'-(3-tolyl)amino]-3,3'-dimethylbiphenyl (HMTPD), and/or mCP.

The thickness of the hole transport region (HTR) may be from about 100 Å to about 10000 Å, for example, from about 100 Å to about 5000 Å. The thickness of the hole injection region (HIL) may be, for example, from about 30 Å to about 1000 Å, and the thickness of the hole transport layer (HTL) may be from about 30 Å to about 1000 Å. For example, the thickness of the electron blocking layer (EBL) may be from about 10 Å to about 1000 Å. If the thicknesses of the hole transport region (HTR), the hole injection layer (HIL), the hole transport layer (HTL) and the electron blocking layer (EBL) satisfy the above-described ranges, a suitable or satisfactory degree of hole transport properties may be achieved without substantial increase of a driving voltage.

The hole transport region (HTR) may further include a charge generating material in addition to the above-described materials to increase conductivity. The charge generating material may be dispersed uniformly or non-uniformly in the hole transport region (HTR). The charge generating material may be, for example, a p-dopant. The p-dopant may be one of quinone derivatives, metal oxides, or cyano group-containing compounds, without limitation. For example, non-limiting examples of the p-dopant may include quinone derivatives such as tetracyanoquinodimethane (TCNQ) and/or 2,3,5,6-tetrafluoro-7,7,8,8-tetracyanoquinodimethane (F4-TCNQ), metal oxides such as tungsten oxide and/or molybdenum oxide, etc., without limitation.

As described above, the hole transport region (HTR) may further include at least one among a hole buffer layer and an electron blocking layer (EBL) in addition to the hole injection layer (HIL) and the hole transport layer (HTL). The hole buffer layer may compensate an optical resonance distance according to the wavelength of light emitted from an emission layer (EML) and may increase light emission efficiency. Materials which may be included in a hole transport region (HTR) may be used as materials included in the hole buffer layer.

The emission layer (EML) is provided on the hole transport region (HTR). The emission layer (EML) may have a thickness of, for example, about 100 Å to 600 Å. The emission layer (EML) may have a single layer formed using a single material, a single layer formed using a plurality of different materials, or a multilayer structure having a plurality of layers formed using a plurality of different materials.

The emission layer (EML) may emit one among red light, green light, blue light, white light, yellow light and cyan light. The emission layer (EML) may include a fluorescence emitting material and/or a phosphorescence emitting material.

In an embodiment, the emission layer (EML) may be a fluorescence emission layer. For example, a portion of light emitted from the emission layer (EML) may be by thermally activated delayed fluorescence (TADF). Particularly, the emission layer (EML) may include a light-emitting component emitting thermally activated delayed fluorescence, and in an embodiment, the emission layer (EML) may be a thermally activated delayed fluorescence emission layer that emits green light.

In the organic electroluminescence device (10) of an embodiment, the emission layer (EML) includes a spiro compound containing an aryl amine group and an indenoindole derivative.

In an embodiment, the emission layer (EML) may include a host and a dopant, and the dopant may include the spiro compound containing the aryl amine group and the indenoindole derivative.

In an embodiment, in the spiro compound, the indenoindole derivative and a pentagonal or hexagonal ring of the spiro compound may form a spiro bond, and the indenoindole derivative and the aryl amine group may be bonded to each other via a linker or via a direct linkage. For example, the indenoindole derivative and the pentagonal or hexagonal ring of the spiro compound may be combined together to form a spiro center (e.g., the indenoindole derivative and the pentagonal or hexagonal ring of the spiro compound may be connected to one another via a spiro atom).

In the present description, -* means a position to be connected.

In the present description, the term "direct linkage" may mean a single bond.

In the present description, the term "substituted or unsubstituted" corresponds to substituted or unsubstituted with one or more substituents selected from the group consisting of a deuterium atom, a halogen atom, a cyano group, a nitro group, an amino group, a silyl group, a boron group, a phosphine oxide group, a phosphine sulfide group, an alkyl group, an alkenyl group, an aryl group and a heterocyclic group. In addition, each of the disclosed substituents may be substituted or unsubstituted. For example, a biphenyl group may be interpreted as an aryl group or a phenyl group substituted with a phenyl group.

In the present description, the term "forming a ring via the combination with an adjacent group" may mean forming a substituted or unsubstituted hydrocarbon ring, or a substituted or unsubstituted heterocycle via the combination with an adjacent group. The hydrocarbon ring includes an aliphatic hydrocarbon ring and an aromatic hydrocarbon ring. The heterocycle includes an aliphatic heterocycle and an aromatic heterocycle. The ring formed by the combination with an adjacent group may be a monocyclic ring or a polycyclic ring. In addition, the ring formed via the combination with an adjacent group may be combined with another ring to form a spiro structure.

In the present description, the term "adjacent group" may mean a substituent substituted for an atom which is directly combined with an atom substituted with a corresponding substituent, another substituent substituted for an atom which is substituted with a corresponding substituent, or a substituent sterically adjacent to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other.

In the present description, examples of the halogen atom may include a fluorine atom, a chlorine atom, a bromine atom or an iodine atom.

In the present description, the alkyl group may be a chain type or a cyclic type (e.g., a linear alkyl group or a cyclic alkyl group) unless otherwise classified. The carbon number of the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present description, the term "aryl group" means an optional functional group or substituent derived from an aromatic hydrocarbon ring. The aryl group may be a monocyclic aryl group or a polycyclic aryl group. The carbon number for forming rings in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc., but embodiments are not limited thereto.

In the present description, the fluorenyl group may be substituted, and two substituents may be combined with each other to form a spiro structure. Examples of a substituted fluorenyl group are as follows. However, embodiments are not limited thereto.

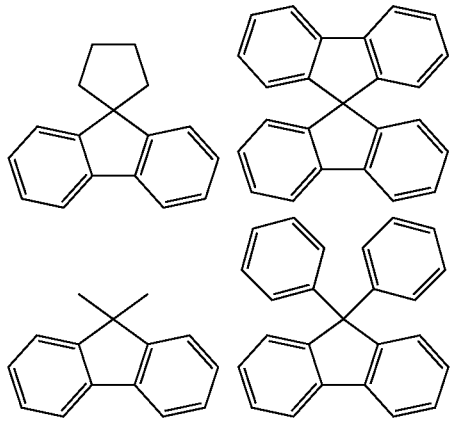

In the present description, the heteroaryl group may include one or more among O, N, P, Si and S as heteroatoms. The ring-forming carbon number of the heteroaryl group may be 2 to 30 or 2 to 20. The heteroaryl group may be a monocyclic heteroaryl group or a polycyclic heteroaryl group. The polycyclic heteroaryl group may have, for example, a two-ring or three-ring structure. Examples of the heteroaryl group may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidyl, pyrido pyrazinyl, pyrazino pyrazinyl, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophenyl, thienothiophene, benzofuranyl, phenanthroline, thiazolyl, isooxazolyl, oxadiazolyl, thiadiazolyl, benzothiazolyl, phenothiazinyl, dibenzosilole, dibenzofuranyl, etc., without limitation.

In the present description, the silyl group includes an alkyl silyl group and an aryl silyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc. However, embodiments are not limited thereto.

In the present description, the carbon number of the amine group is not specifically limited, but may be 1 to 30. The amine group may include an alkyl amine group and an aryl amine group. Examples of the amine group include a methylamine group, a dimethylamine group, a phenylamine group, a naphthylamine group, a 9-methyl-anthracenylamine group, a triphenylamine group, etc., without limitation.

Referring to FIG. 1 to FIG. 3 again, the emission layer (EML) may include a spiro compound represented by Formula 1 below.

Formula 1

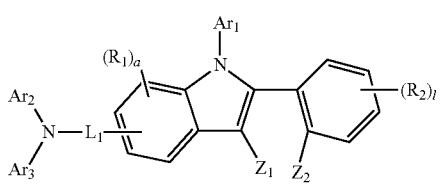

In Formula 1, $R_1$ and $R_2$ may be each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, or combined with an adjacent group to form a ring.

In Formula 1, $Ar_1$ may be a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms.

In an embodiment, in the substituted or unsubstituted $Ar_2$, there may be one to eight substituents, and in a case of two or more substituents, the substituents may be the same or different.

In an embodiment, in a case of one or more substituents of $Ar_1$, the substituent of $Ar_1$ may be a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms.

In an embodiment, $Ar_1$ may be a substituted or unsubstituted phenyl group, a substituted or unsubstituted pyridyl group, a substituted or unsubstituted pyrimidyl group, or a substituted or unsubstituted triazinyl group.

In Formula 1, $Ar_2$ and $Ar_3$ may be each independently a substituted or unsubstituted aryl group of 6 to 30 ring-forming carbon atoms, or a substituted or unsubstituted heteroaryl group of 2 to 30 ring-forming carbon atoms.

The spiro compound according to the present disclosure includes an aryl amine group, and a core structure itself has a twisted stereostructure. Due to such steric effects, a triplet energy level value may increase, and the absolute value ($\Delta Est$) of a difference between a singlet energy level and a triplet energy level may decrease.

In Formula 1, $L_1$ may be a direct linkage, a substituted or unsubstituted arylene group of 6 to 30 ring-forming carbon atoms, or a substituted or unsubstituted heteroarylene group of 2 to 30 ring-forming carbon atoms.

In an embodiment, $L_1$ may be a direct linkage.

In Formula 1, a is an integer of 0 to 3, and l is an integer of 0 to 4. Meanwhile, if a is 2 or more, multiple $R_1$ groups are the same or different, and if l is 2 or more, multiple $R_2$ groups are the same or different.

In Formula 1, $Z_1$ and $Z_2$ form spiro bonds with a ring compound represented by Formula 2 below. For example, $Z_1$ and $Z_2$ may both be bonded to the same spiro atom or spiro center.

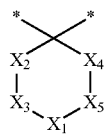

Formula 2

In Formula 2, $X_1$ may be a direct linkage, O, S, $CR_5R_6$, $SiR_7R_8$, $BR_9$, or $NR_{10}$.

In Formula 2, $X_2$ to $X_5$ may be each independently $CR_{11}R_{12}$.

In Formula 2, $R_5$ to $R_{12}$ may be each independently a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, and * indicates a binding site to an adjacent atom of Formula 1.

In the spiro compound according to the present disclosure, $Z_1$ and $Z_2$ of Formula 1 and a ring compound represented by Formula 2 form spiro bonds (e.g., $Z_1$ and $Z_2$ may both be bonded to the same spiro atom or spiro center), and accordingly, $sp^3$ carbon of fluorene may be protected, durability at a high temperature may become excellent, and thermal decomposition under high temperature conditions may be difficult to occur, and the life of a device may increase.

In an embodiment, Formula 2 may be represented by any one among Formula 2-1 to Formula 2-7 below.

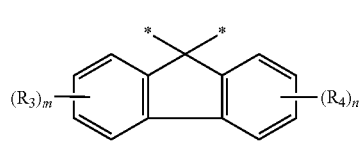

Formula 2-1

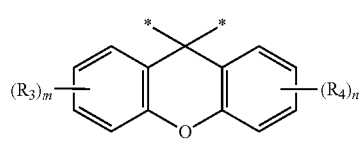

Formula 2-2

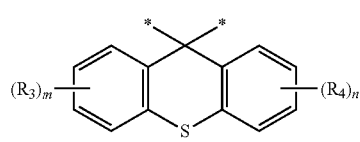

Formula 2-3

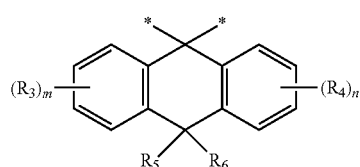

Formula 2-4

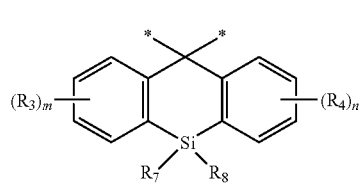

Formula 2-5

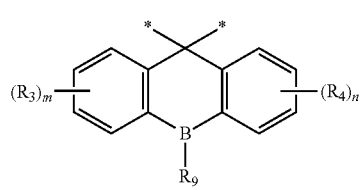

Formula 2-6

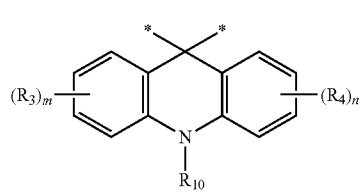

Formula 2-7

In Formula 2-1 to Formula 2-7, $R_3$ and $R_4$ may be each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, or combined with an adjacent group to form a ring, and * indicates a binding site to an adjacent atom of Formula 1.

In Formula 2-1 to Formula 2-7, m and n are each independently an integer of 0 to 4. Meanwhile, if m is 2 or more, multiple $R_3$ groups are the same or different, and if n is 2 or more, multiple $R_4$ groups are the same or different.

Formula 2-1 represents Formula 2 where $X_1$ is a direct linkage, Formula 2-2 represents Formula 2 where $X_1$ is O, Formula 2-3 represents Formula 2 where $X_1$ is S, Formula 2-4 represents Formula 2 where $X_1$ is $CR_5R_6$, and Formula 2-5 represents Formula 2 where $X_1$ is $SiR_7R_8$. In addition, Formula 2-6 represents Formula 2 where $X_1$ is $BR_9$, and Formula 2-7 represents Formula 2 where $X_1$ is $NR_{10}$.

Meanwhile, in Formula 2-1 to Formula 2-7, the same explanation on $R_5$ to $R_{10}$ referring to Formula 2 may be applied.

In an embodiment, Formula 1 may be represented by Formula 3 below.

Formula 3

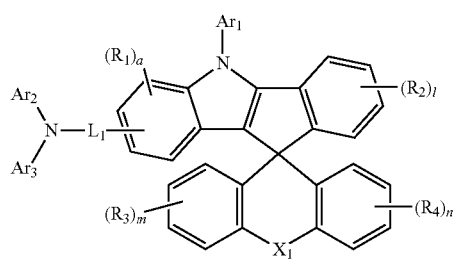

In Formula 3, $R_3$ and $R_4$ may be each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, or combined with an adjacent group to form a ring.

In Formula 3, m and n are each independently an integer of 0 to 4. Meanwhile, if m is 2 or more, multiple $R_3$ groups are the same or different, and if n is 2 or more, multiple $R_4$ groups are the same or different.

In Formula 3, $R_1$, $R_2$, $R_5$ to $R_{10}$, $Ar_1$ to $Ar_3$, $L_1$, $X_1$, a, and l are the same as defined in Formula 1 and Formula 2.

Formula 3 may be represented by any one among Formula 3-1 to Formula 3-5 below.

Formula 3-1

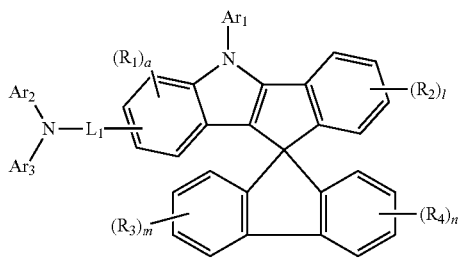

Formula 3-2

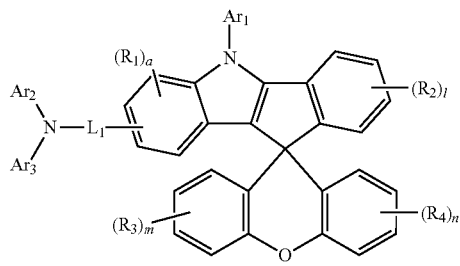

Formula 3-3

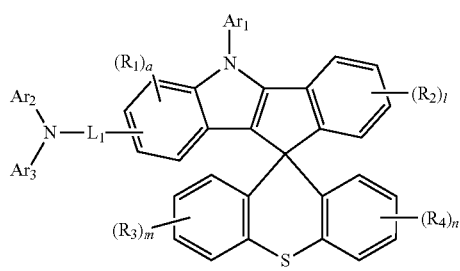

Formula 3-4

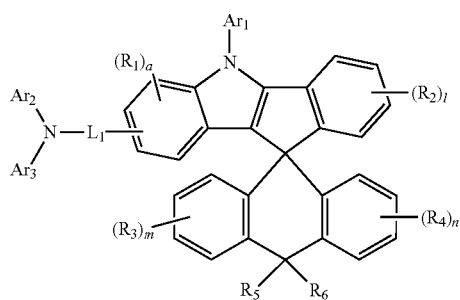

Formula 3-5

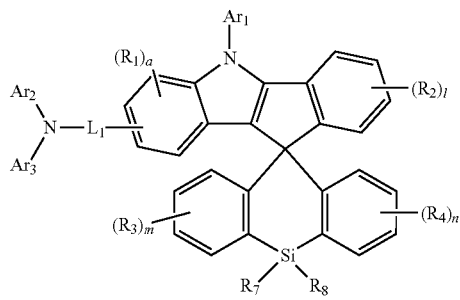

In Formulae 3-1 to 3-5, $R_1$ to $R_8$, $Ar_1$ to $Ar_3$, $L_1$, a, and l to n are the same as defined in Formula 3.

In an embodiment, Formula 3 may be represented by Formula 4-1 or Formula 4-2 below.

The spiro compound represented by Formula 1 may be represented by any one among the compounds represented in Compound Group 1 below.

Compound Group 1

Formula 4-1

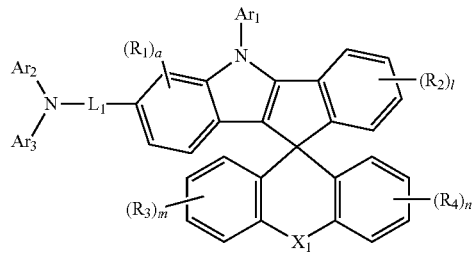

Formula 4-2

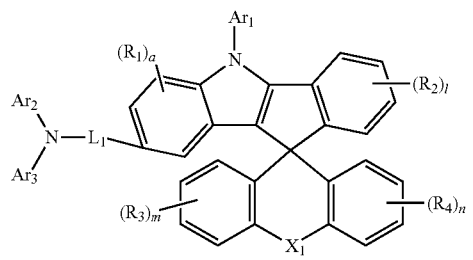

In Formulae 4-1 and 4-2, $X_1$, $R_1$ to $R_8$, $Ar_1$ to $Ar_3$, $L_1$, a, and l to n are the same as defined in Formula 3.

The spiro compound of an embodiment, represented by Formula 1 may be a material emitting delayed fluorescence. The spiro compound of an embodiment may be a material emitting thermally activated delayed fluorescence.

The spiro compound of an embodiment, represented by Formula 1 may have an absolute value (ΔEst) of a difference between a singlet energy level (S1) and a triplet energy level (Ti) of 0.2 eV or less. For example, S1-T1≤0.2 eV may be satisfied.

For example, the spiro compound represented by Formula 1 has a small difference between a singlet energy level (S1) and a triplet energy level (T1), and may be used as a material emitting thermally activated delayed fluorescence. Particularly, the spiro compound represented by Formula 1 may be used as a green light emitting material which emits thermally activated delayed fluorescence. However, embodiments are not limited thereto, and the spiro compound of an embodiment may be a material emitting thermally activated delayed fluorescence emitting blue light or red light.

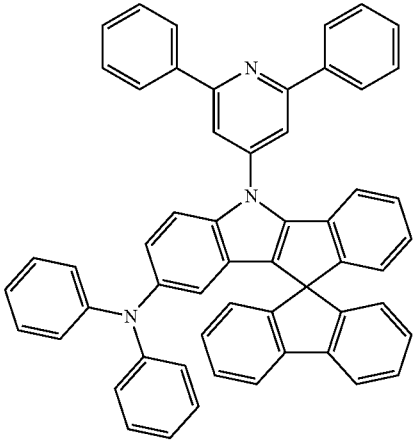

1

2

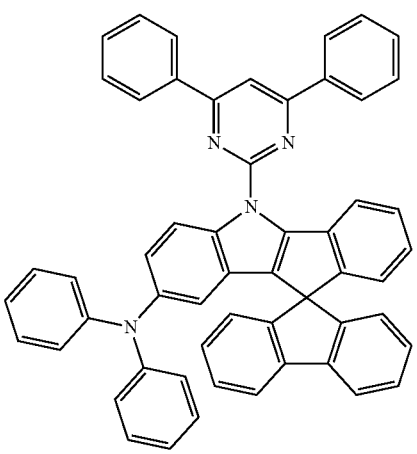 [SMILES: c1ccc(-c2nc(-c3ccccc3)nc(-n3c4c(c5cc(N(c6ccccc6)c6ccccc6)ccc53)C3(c5ccccc5-c5ccccc53)c3ccccc3-4)n2)cc1]

3

4
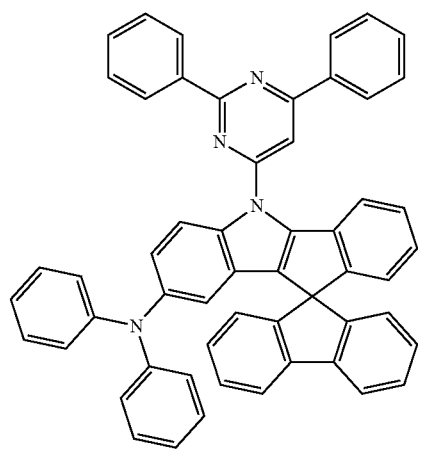
5
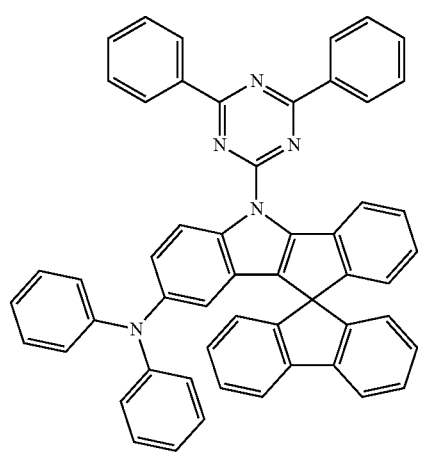
6
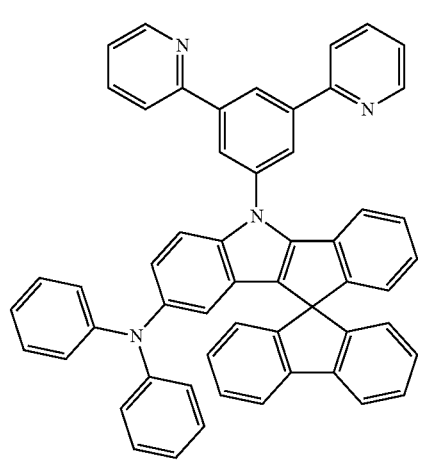
7
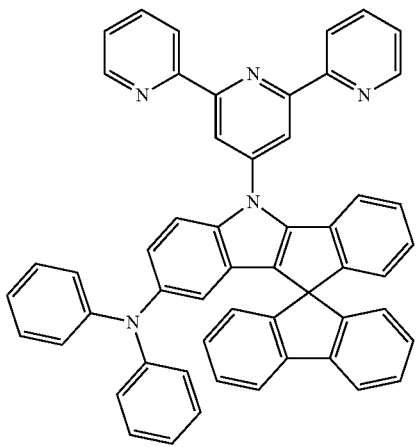
8
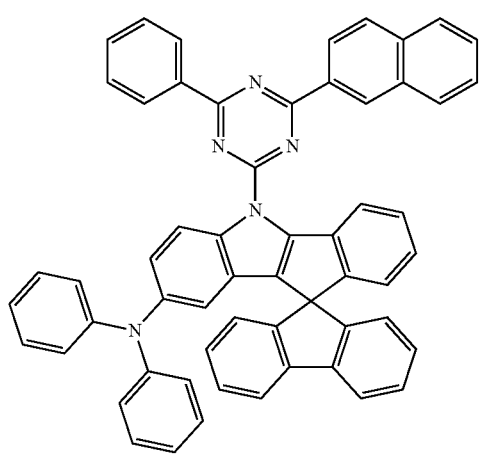
9
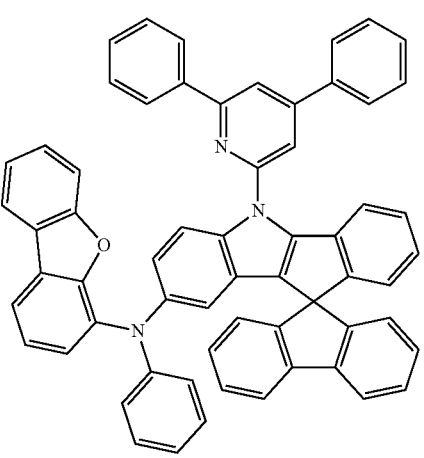

10
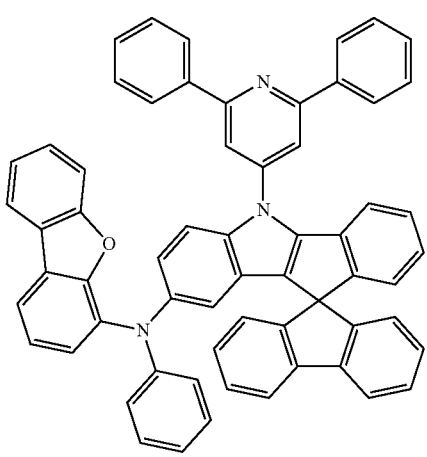
11
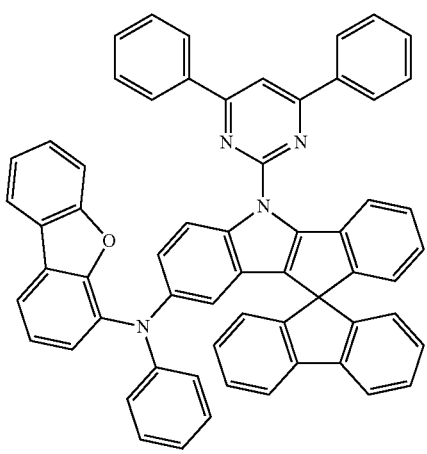
12
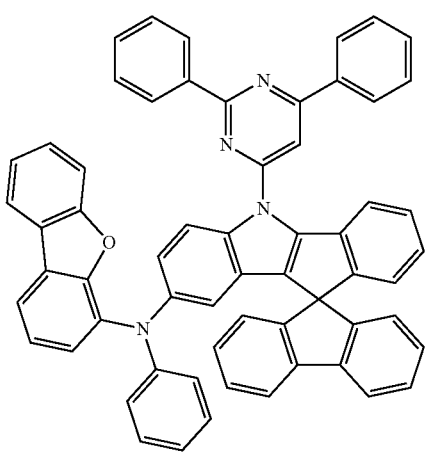
13
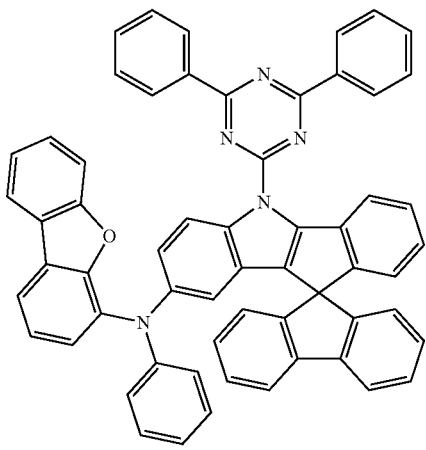
14
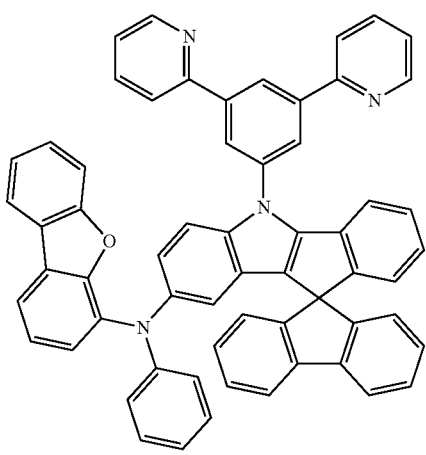
15
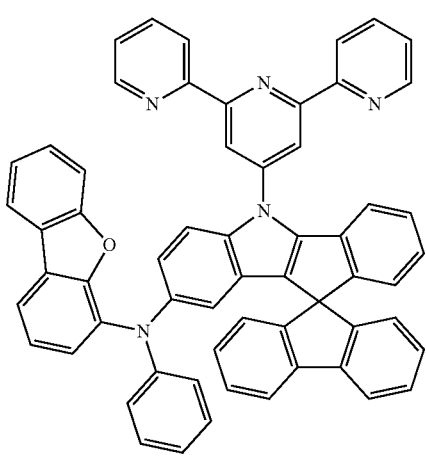

16
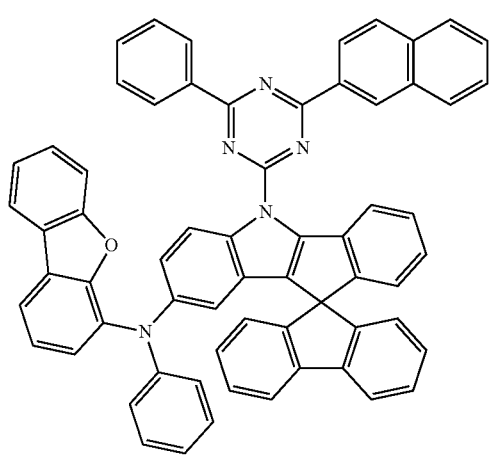
17
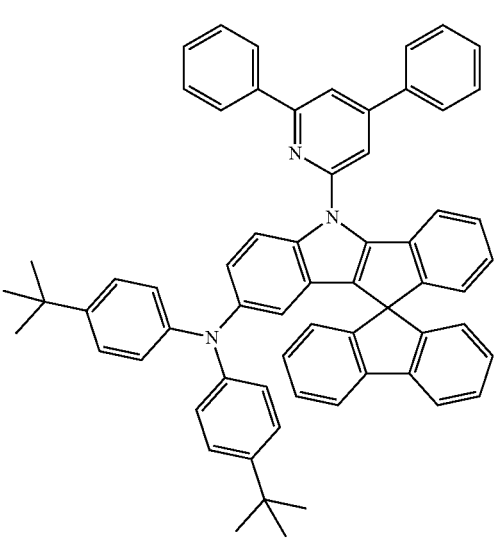
18
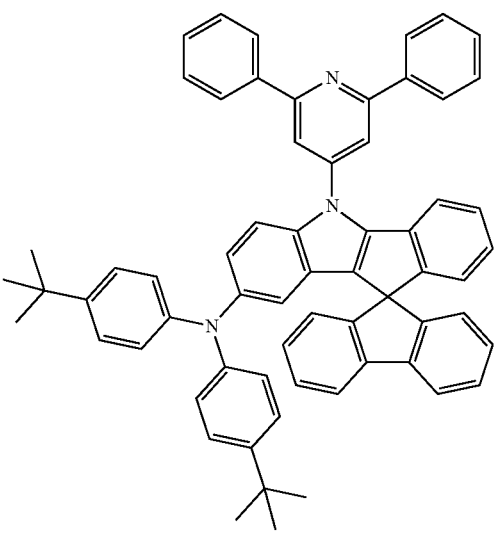
19
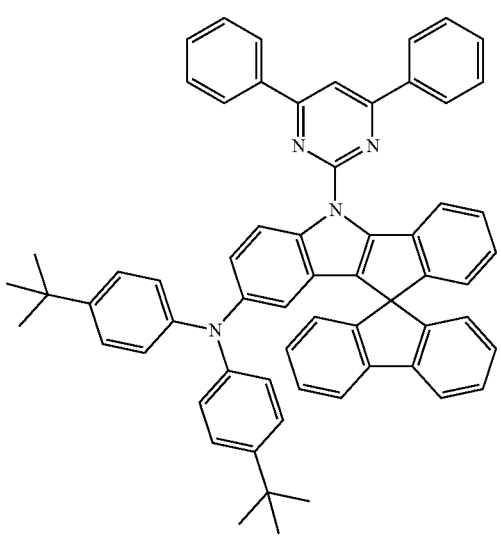 [SMILES: CC(C)(C)c1ccc(N(c2ccc(C(C)(C)C)cc2)c2ccc3c(c2)c2c(n3-c3nc(-c4ccccc4)nc(-c4ccccc4)n3)-c3ccccc3C23c2ccccc2-c2ccccc23)cc1]
20
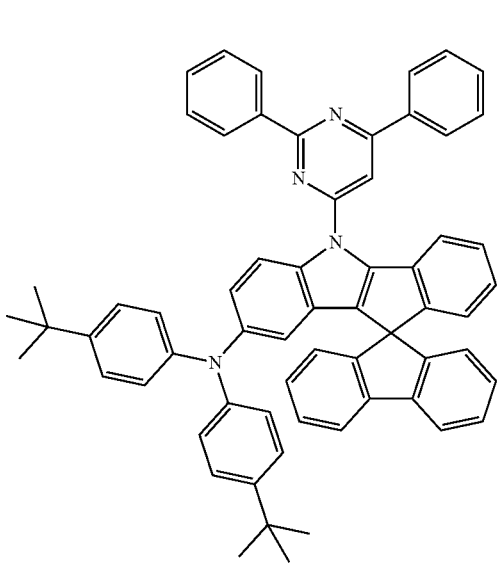
21
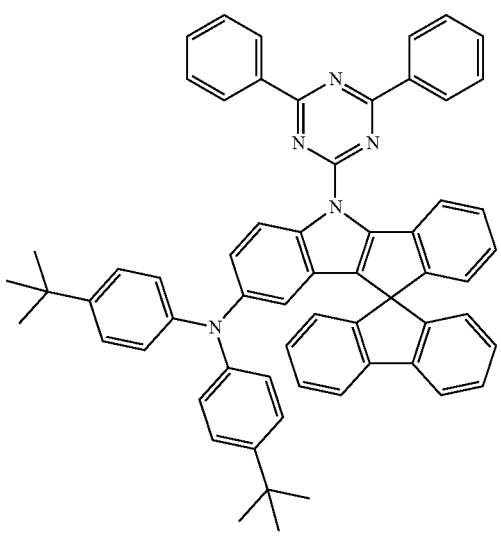

-continued
22
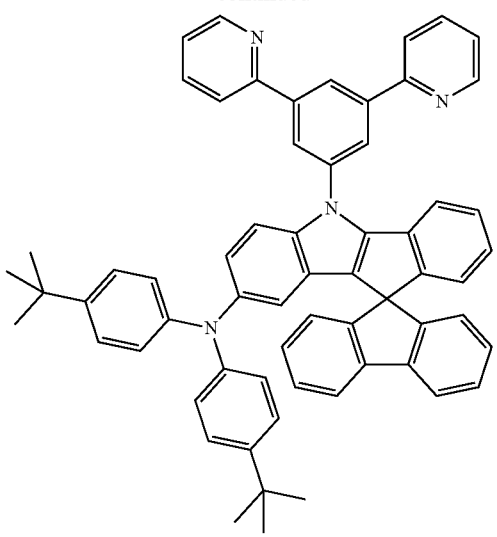
23
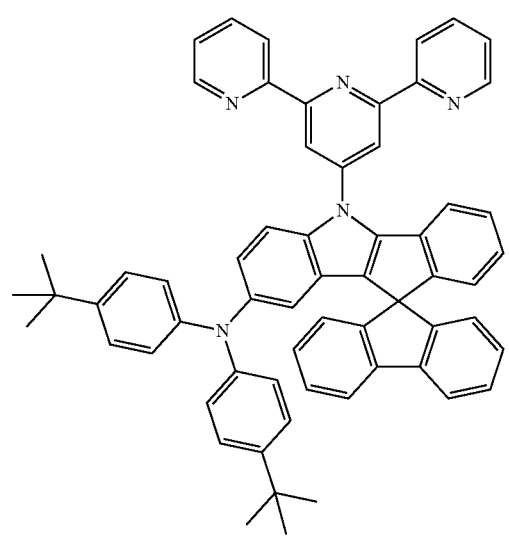
24
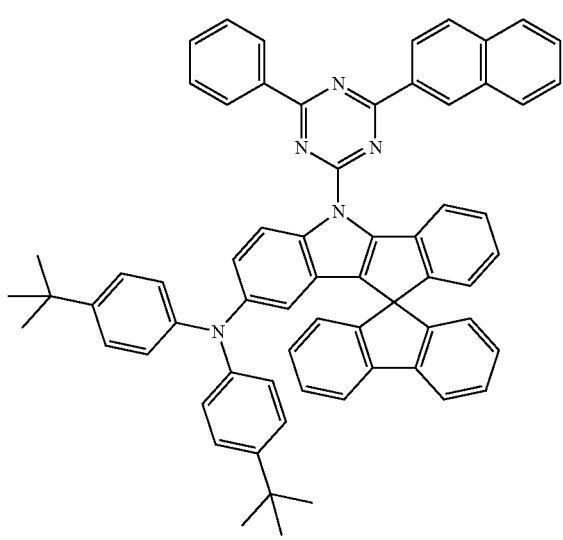
-continued
25
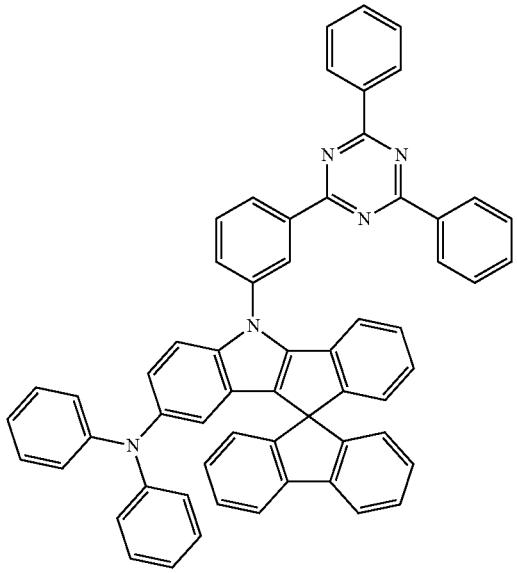
26
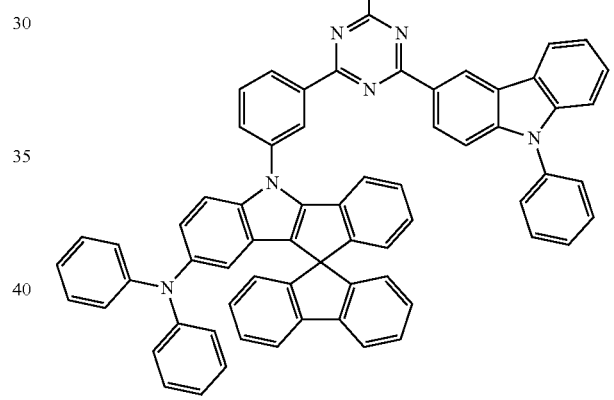
27
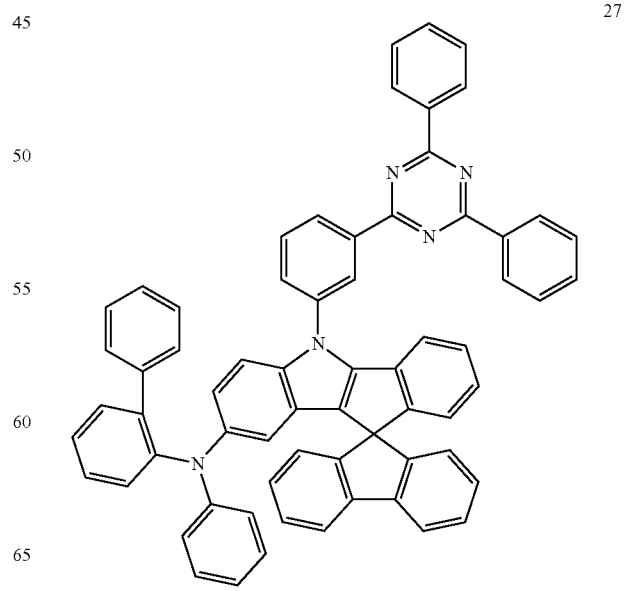

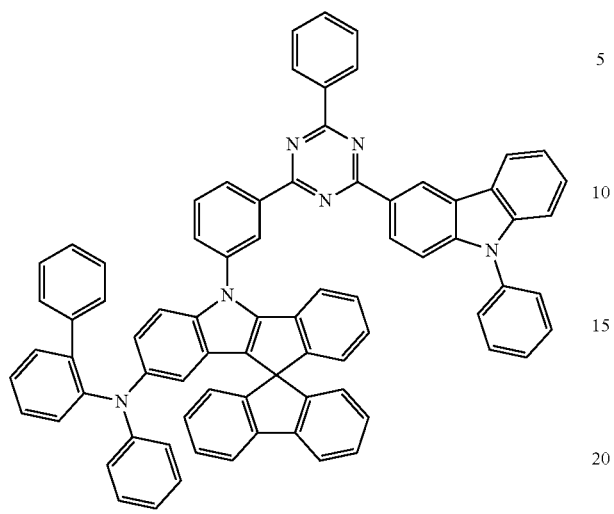
28
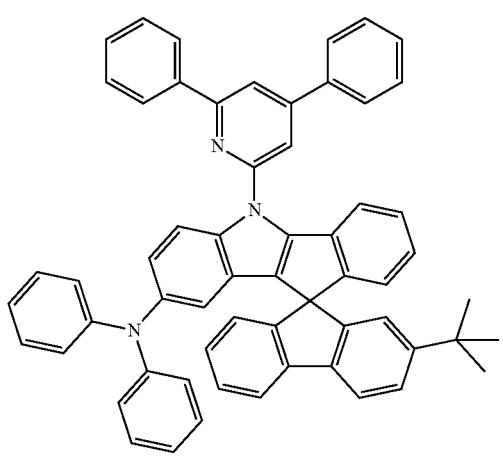
29
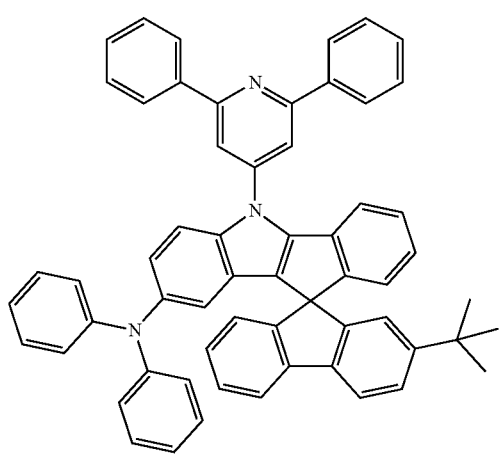
30
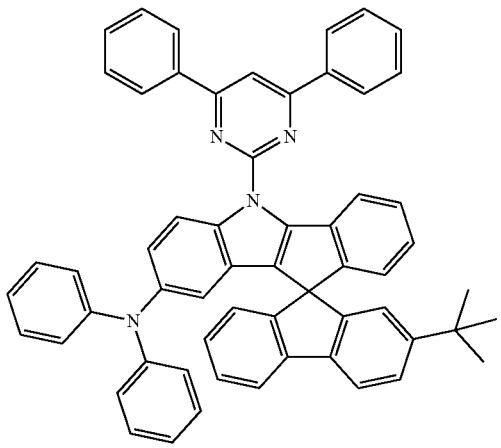
31
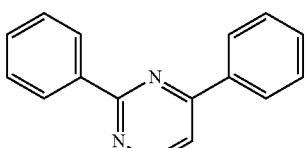
32
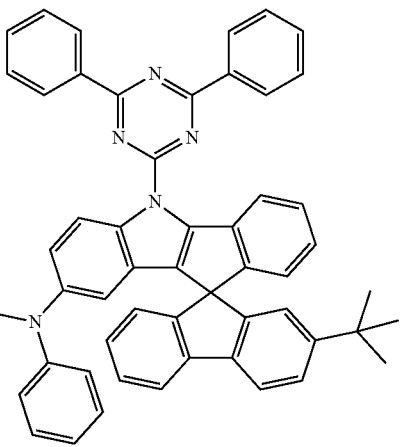
33

34
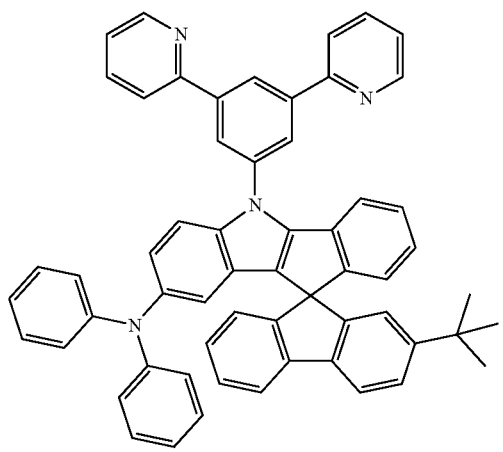
35
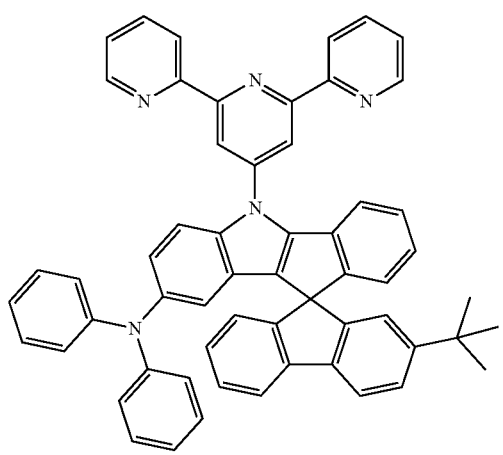
36
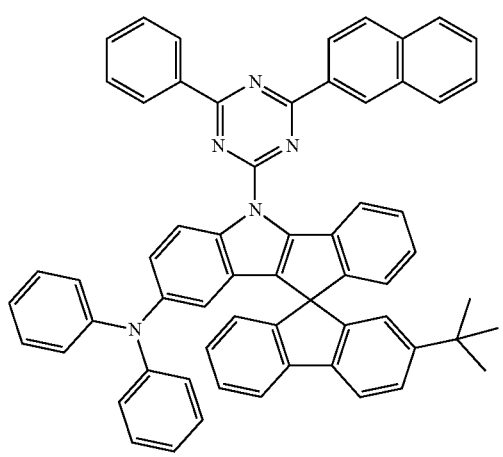
37
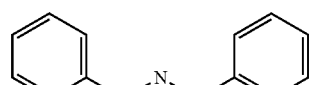
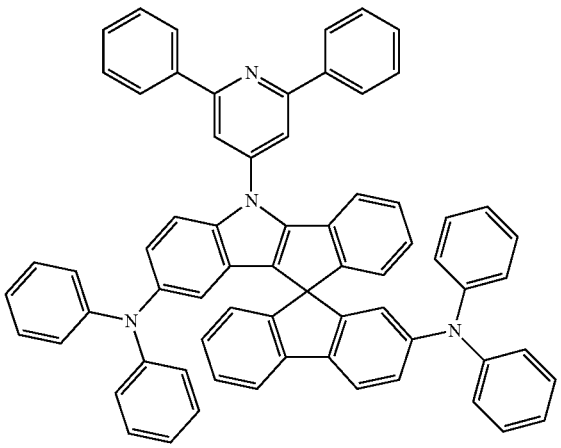
38
39
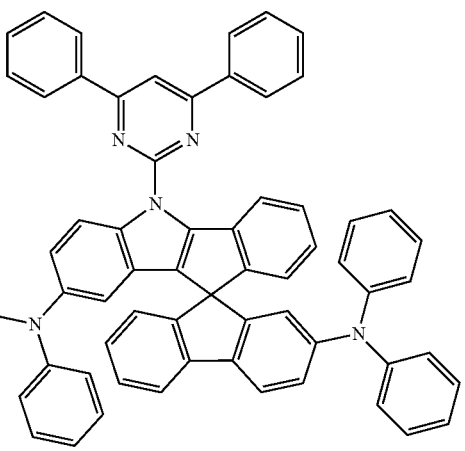

40
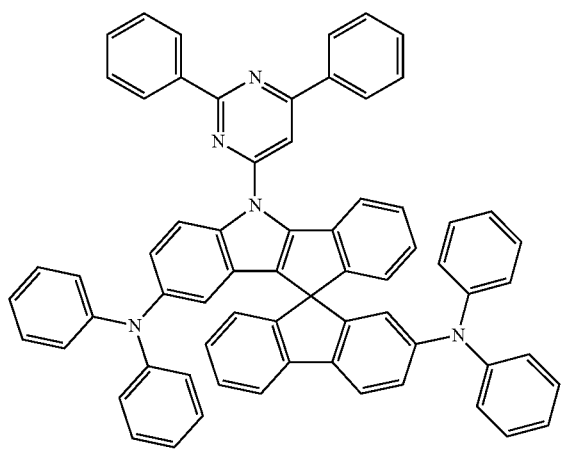
41
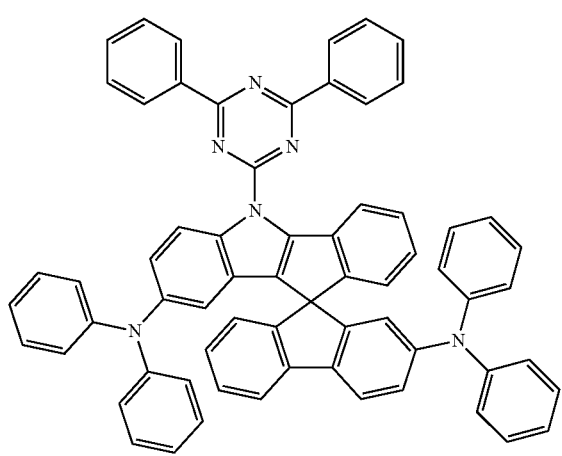
42
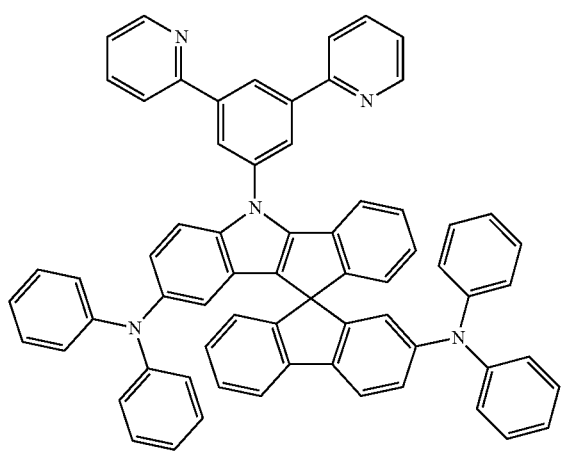
43
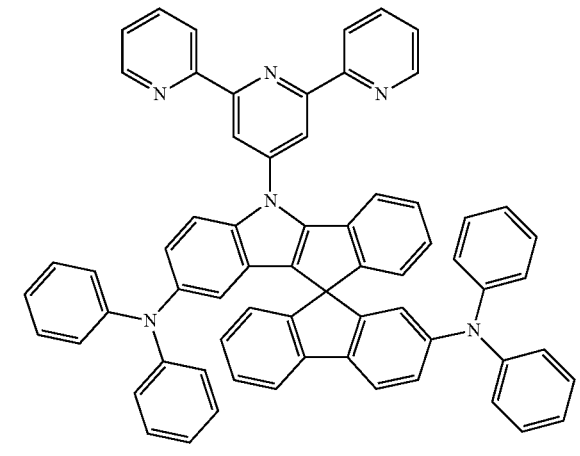
44
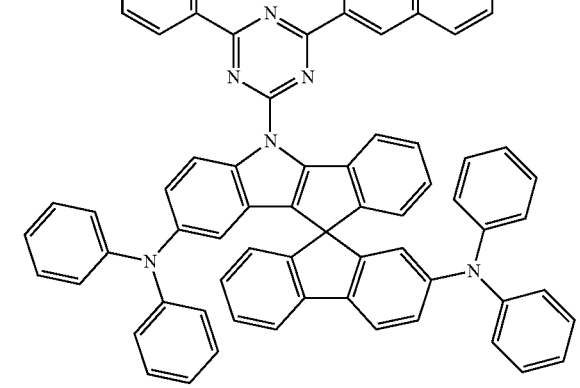
45
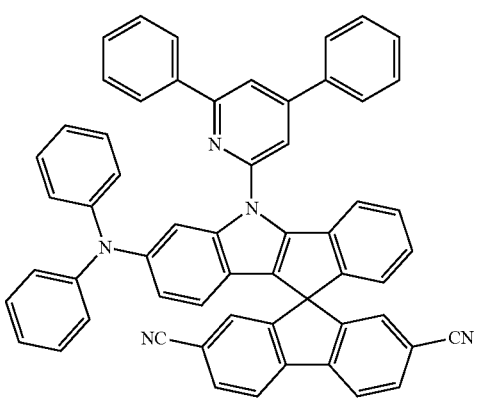

46
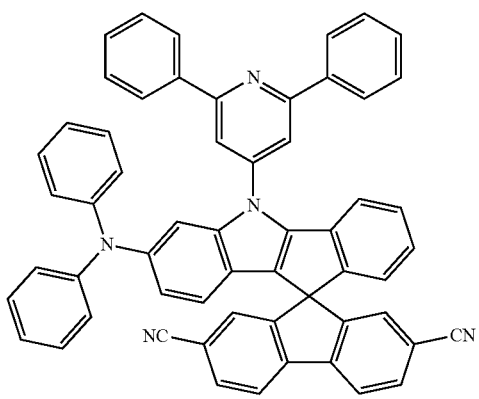
47
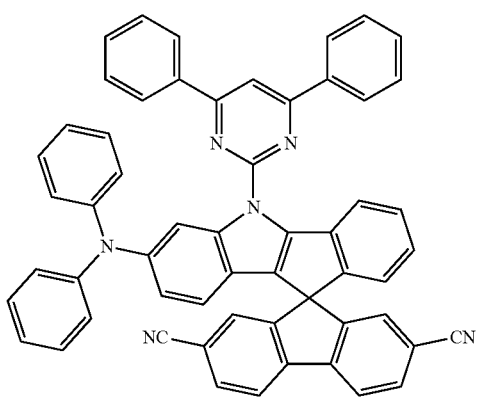
48
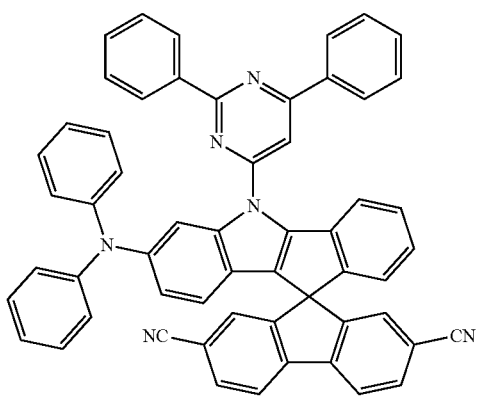
49
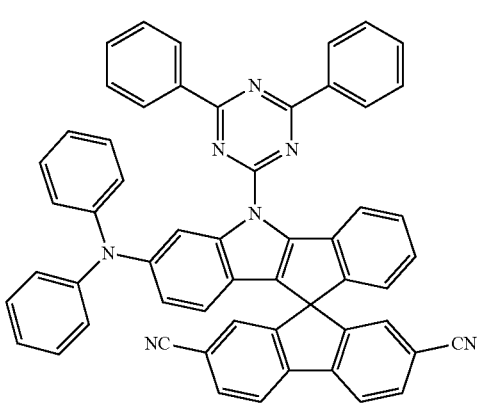
50
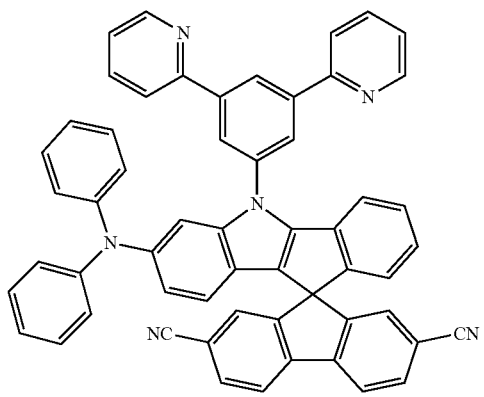
51
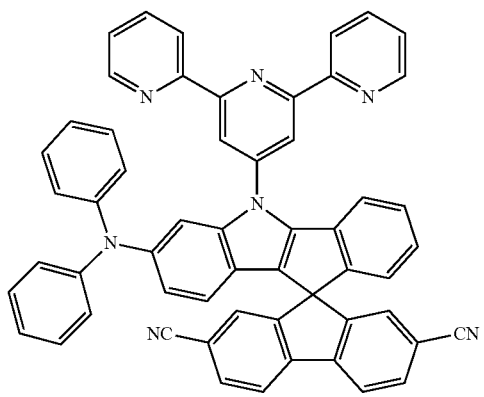
52
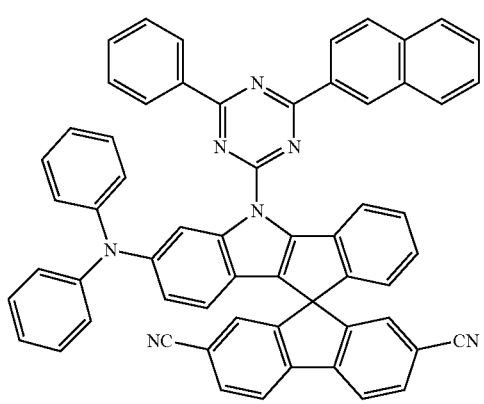
53
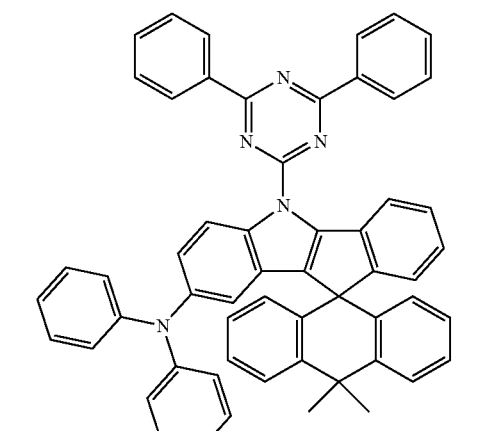

54
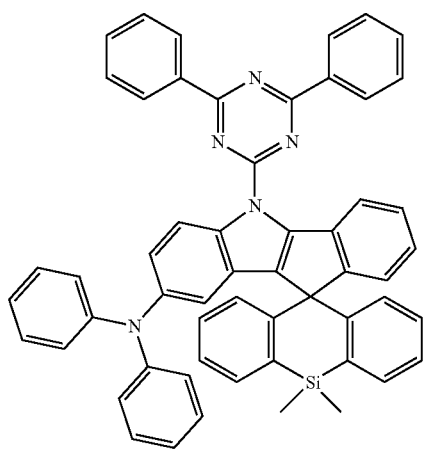
55
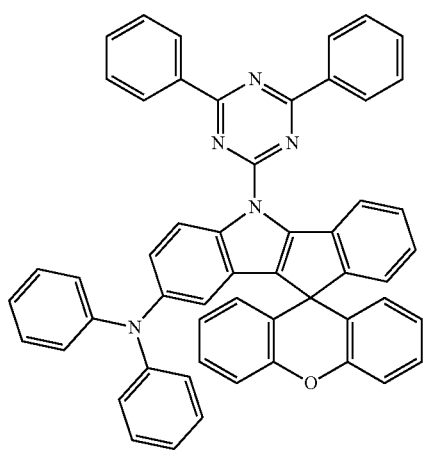
56
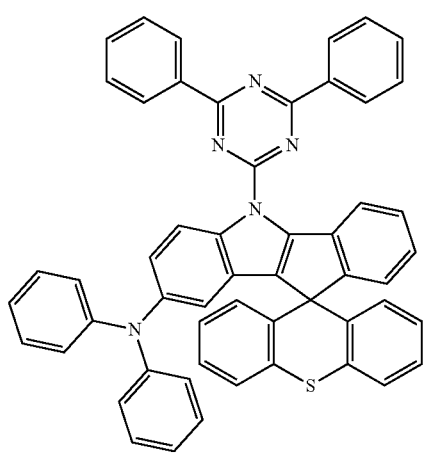
57
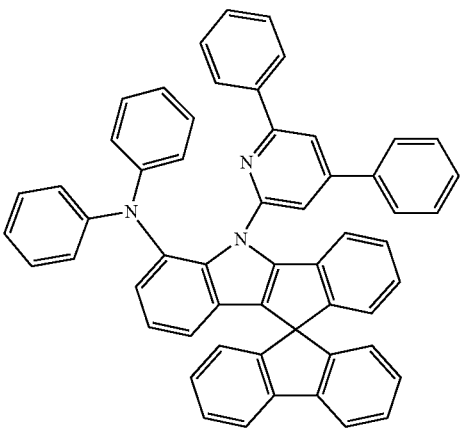
58
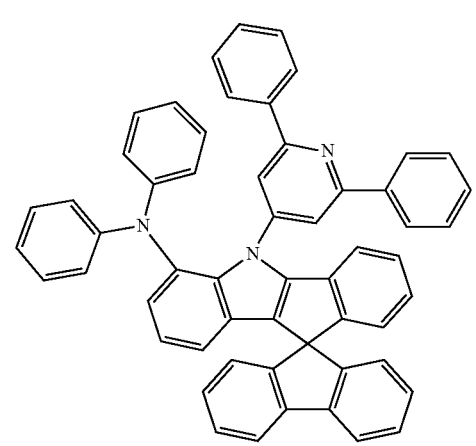
59
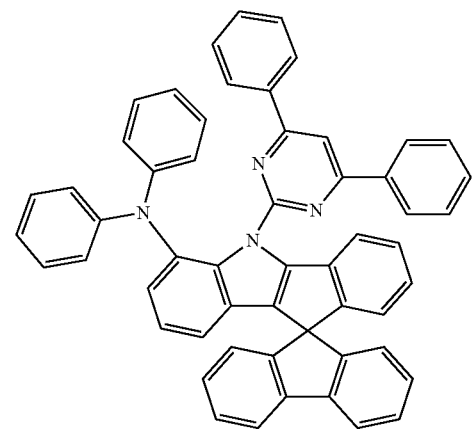

37
-continued
60
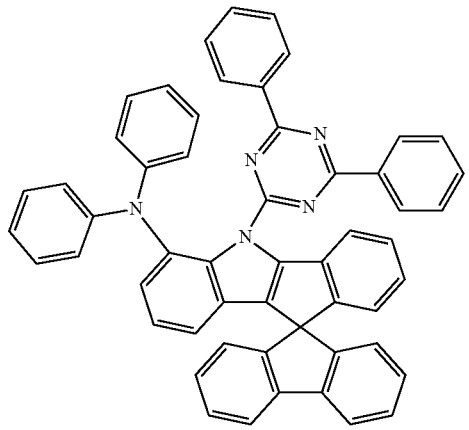
61
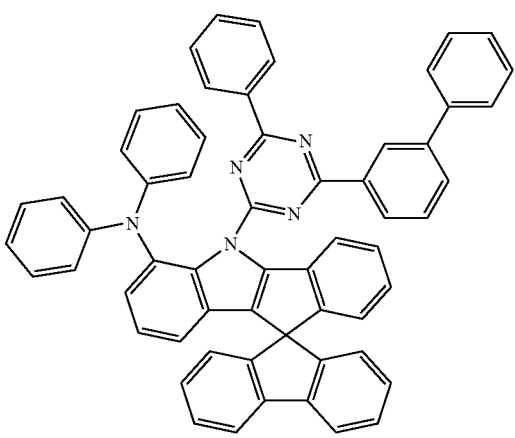
62
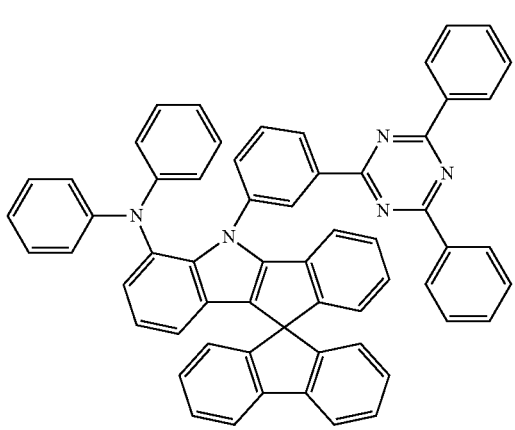
38
-continued
63
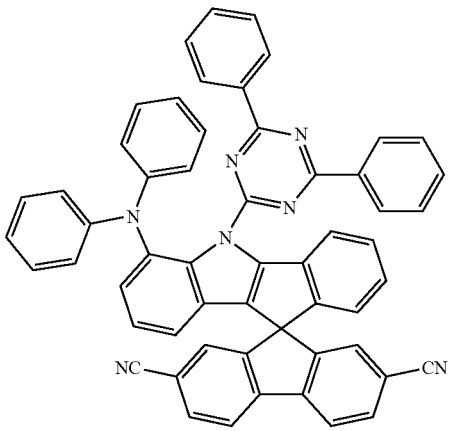
64
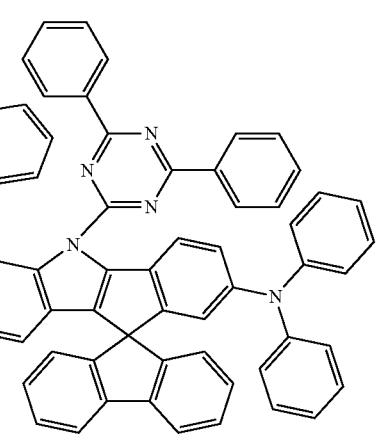
65
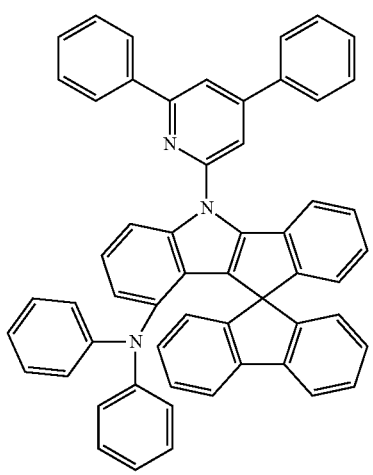

66
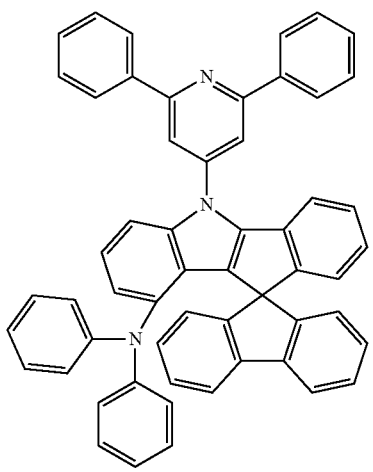
67
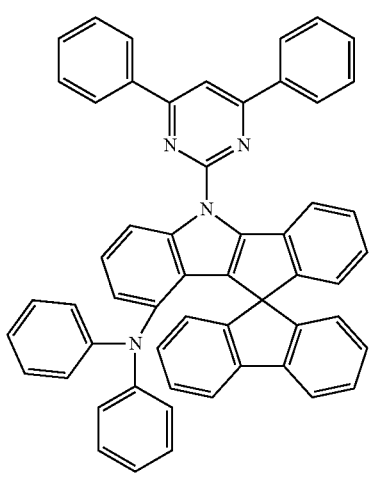
68
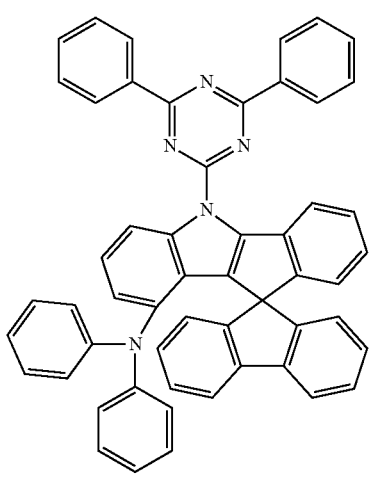
69
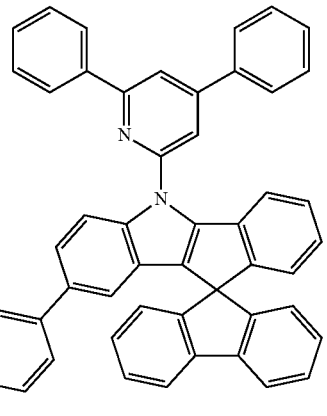
70
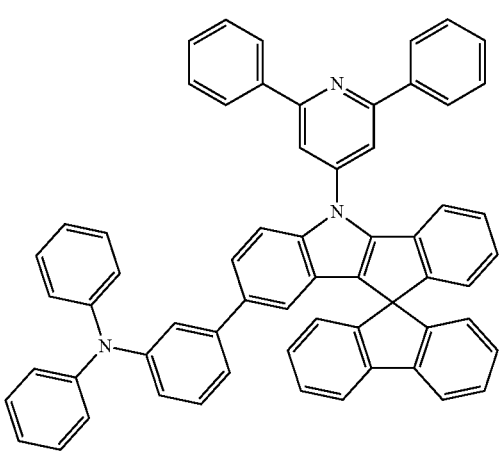
71
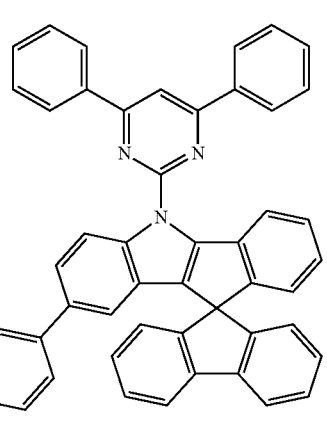

41
-continued
72
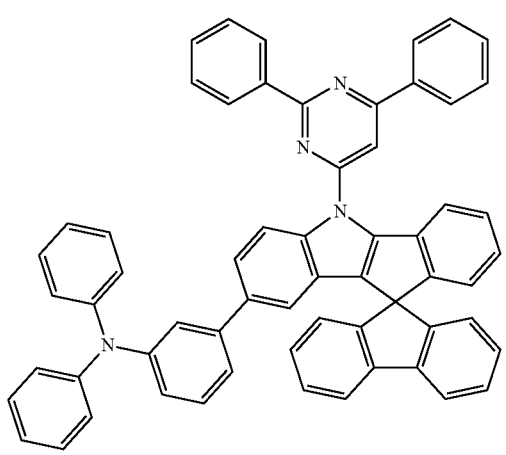
73
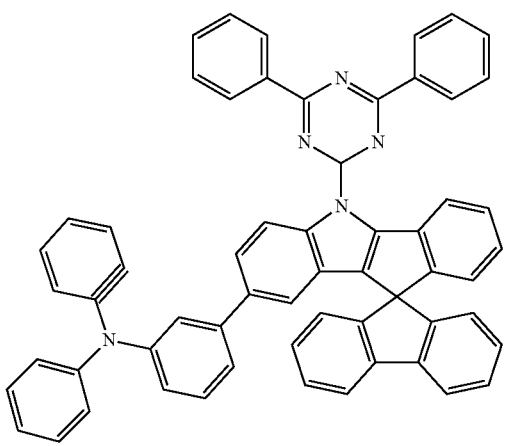
74
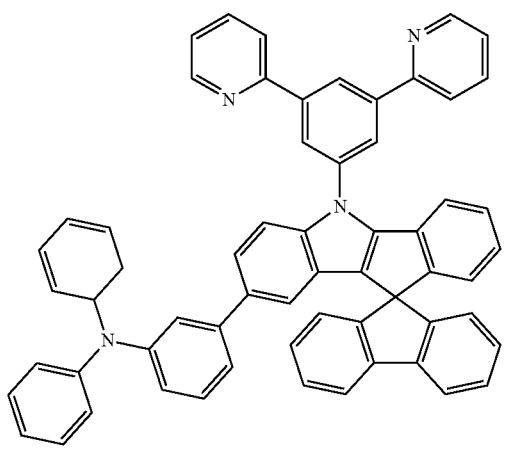
42
-continued
75
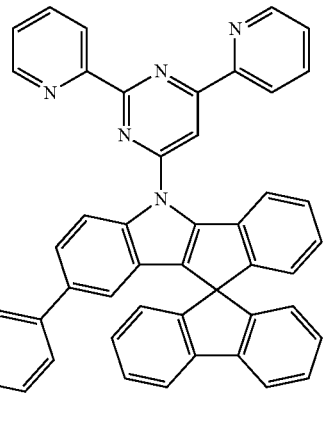
76
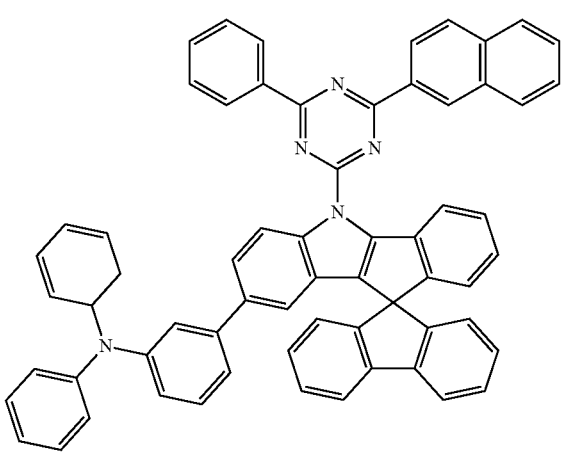
77
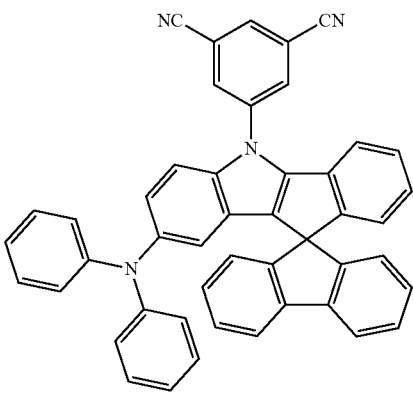

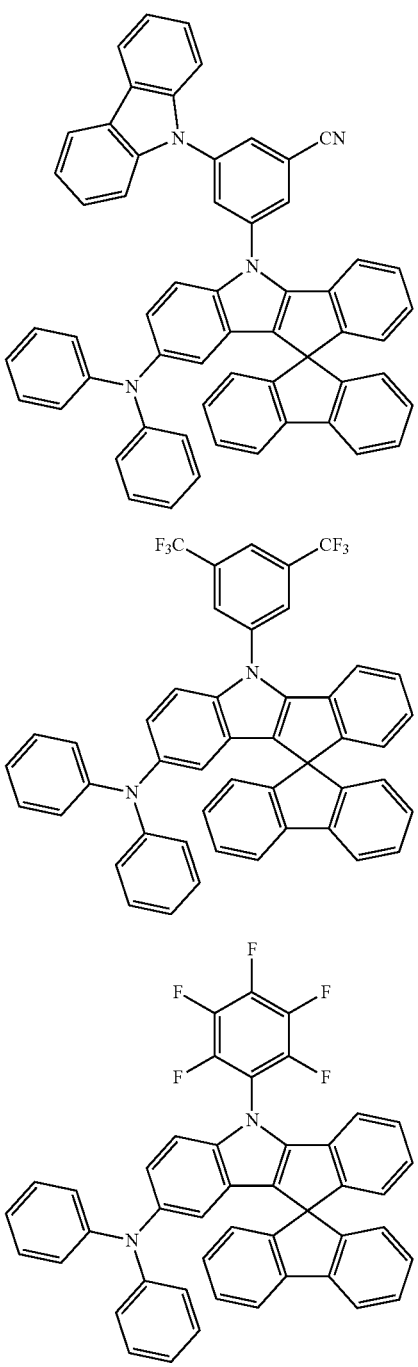

The spiro compound represented by Formula 1 may be used in the organic electroluminescence device (10) of an embodiment and may improve the efficiency and life of the organic electroluminescence device. Particularly, the spiro compound represented by Formula 1 may be used in the emission layer (EML) of the organic electroluminescence device (10) of an embodiment and may improve the emission efficiency and life of the organic electroluminescence device.

In an embodiment, the emission layer (EML) includes a host and a dopant, the host may be a host for emitting delayed fluorescence, and the dopant may be a dopant emitting delayed fluorescence. Meanwhile, the spiro compound of an embodiment, represented by Formula 1 may be included as the dopant material of the emission layer (EML). For example, the spiro compound of an embodiment, represented by Formula 1 may be used as a TADF dopant.

In an embodiment, the emission layer (EML) may include any suitable host material used in the art. For example, in an embodiment, the emission layer (EML) may include as a host material, tris(8-hydroxyquinolino)aluminum ($Alq_3$), 4,4'-bis(N-carbazolyl)-1,1'-biphenyl (CBP), poly(n-vinylcarbazole) (PVK), 9,10-di(naphthalene-2-yl)anthracene (ADN), 4,4',4"-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), or 2,8-bis(diphenylphosphoryl)dibenzofuran (PPF), etc. However, embodiments are not limited thereto, and any suitable host materials used in the art for emitting delayed fluorescence other than the suggested host materials may be included.

Meanwhile, in the organic electroluminescence device (10) of an embodiment, the emission layer (EML) may include any suitable dopant material used in the art. In an embodiment, the emission layer (EML) may include as a dopant, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), and/or N-(4-((E)-2-(6-((E)-4-(diphenylamino)styryl)naphthalen-2-yl) vinyl)phenyl)-N-phenylbenzenamine (N-BDAVBi), perylene and/or derivatives thereof (for example, 2,5,8,11-tetra-t-butylperylene (TBP)), pyrene and/or derivatives thereof (for example, 1,1-dipyrene, 1,4-dipyrenylbenzene, and/or 1,4-bis(N,N-diphenylamino)pyrene), etc.

Referring to FIG. 1 to FIG. 3 again, in the organic electroluminescence device (10) of an embodiment, the electron transport region (ETR) is provided on the emission layer (EML). The electron transport region (ETR) may include at least one of an electron blocking layer, an electron transport layer (ETL) or an electron injection layer (EIL). However, embodiments are not limited thereto.

The electron transport region (ETR) may have a single layer formed using a single material, a single layer formed using a plurality of different materials, or a multilayer structure having a plurality of layers formed using a plurality of different materials.

For example, the electron transport region (ETR) may have a single layer structure of an electron injection layer (EIL) or an electron transport layer (ETL), or a single layer structure formed using an electron injection material and an electron transport material. Further, the electron transport region (ETR) may have a single layer structure having a plurality of different materials, or a structure stacked from the first electrode (EL1) of electron transport layer (ETL)/electron injection layer (EIL), or hole blocking layer/electron transport layer (ETL)/electron injection layer (EIL), without limitation. The thickness of the electron transport region (ETR) may be, for example, from about 100 Å to about 1500 Å.

The electron transport region (ETR) may be formed using various suitable methods such as a vacuum deposition method, a spin coating method, a cast method, a Langmuir- Blodgett (LB) method, an inkjet printing method, a laser printing method, and/or a laser induced thermal imaging (LITI) method.

If the electron transport region (ETR) includes an electron transport layer (ETL), the electron transport region (ETR) may include tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate) (Bebq$_2$), 9,10-di(naphthalene-2-yl)anthracene (ADN), and/or mixtures thereof, but embodiments are not limited thereto.

If the electron transport region (ETR) includes the electron transport layer (ETL), the thickness of the electron transport layer (ETL) may be from about 100 Å to about 1000 Å, for example, from about 150 Å to about 500 Å. If the thickness of the electron transport layer (ETL) satisfies the above-described range, a suitable or satisfactory degree of electron transport properties may be obtained without substantial increase of a driving voltage.

If the electron transport region (ETR) includes the electron injection layer (EIL), the electron transport region (ETR) may include LiF, lithium quinolate (LiQ), Li$_2$O, BaO, NaCl, CsF, a lanthanide metal such as Yb, and/or a metal halide such as RbCl, RbI, and/or KI. However, embodiments are not limited thereto. The electron injection layer (EIL) may also be formed using a mixture material of an electron transport material and an insulating organo metal salt. The organo metal salt may be a material having an energy band gap of approximately 4 eV or more. Particularly, the organo metal salt may include, for example, metal acetates, metal benzoates, metal acetoacetates, metal acetylacetonates, and/or metal stearates.

If the electron transport region (ETR) includes the electron injection layer (EIL), the thickness of the electron injection layer EIL may be from about 1 Å to about 100 Å, and from about 3 Å to about 90 Å. If the thickness of the electron injection layer EIL satisfies the above described range, a suitable or satisfactory degree of electron injection properties may be obtained without inducing substantial increase of a driving voltage.

As described above, the electron transport region (ETR) may include a hole blocking layer. The hole blocking layer may include, for example, at least one among 2,9-dimethyl-4,7-diphenyl-1,10-phenanthroline (BCP), and 4,7-diphenyl-1,10-phenanthroline (Bphen). However, embodiments are not limited thereto.

The second electrode (EL2) is provided on the electron transport region (ETR). The second electrode (EL2) has conductivity. The second electrode (EL2) may be formed using a metal alloy and/or a conductive compound. The second electrode (EL2) may be a cathode. The second electrode (EL2) may be a transmissive electrode, a transflective electrode or a reflective electrode. If the second electrode (EL2) is the transmissive electrode, the second electrode (EL2) may be formed of a transparent metal oxide, for example, indium tin oxide (ITO), indium zinc oxide (IZO), zinc oxide (ZnO), indium tin zinc oxide (ITZO), etc.

If the second electrode (EL2) is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, compounds thereof, and/or mixtures thereof (for example, a mixture of Ag and Mg). Otherwise, a multilayered structure including a reflective layer or a transflective layer formed using the above-described materials and a transparent conductive layer formed using indium tin oxide (ITO), indium zinc oxide (IZO), zinc oxide (ZnO), indium tin zinc oxide (ITZO), etc. may be formed.

Though not shown, the second electrode (EL2) may be coupled with an auxiliary electrode. If the second electrode (EL2) is coupled with the auxiliary electrode, the resistance of the second electrode (EL2) may be reduced.

In the organic electroluminescence device (10), according to the application of voltages to the first electrode (EL1) and the second electrode (EL2), respectively, holes injected from the first electrode (EL1) move via the hole transport region (HTR) to the emission layer (EML), and electrons injected from the second electrode (EL2) move via the electron transport region (ETR) to the emission layer (EML). The electrons and the holes recombine in the emission layer EML to produce excitons, and light is emitted while the excitons fall from excited states to a ground state.

If the organic electroluminescence device (10) is a top emission type, the first electrode (EL1) may be a reflective type electrode, and the second electrode (EL2) may be a transmissive electrode or a transflective electrode. If the organic electroluminescence device (10) is a bottom emission type, the first electrode (EL1) may be a transmissive electrode or a transflective electrode, and the second electrode (EL2) may be a reflective electrode.

The organic electroluminescence device (10) according to an embodiment of the present disclosure uses the above-described spiro compound as a material for an emission layer and may show improved emission efficiency and life characteristics.

An embodiment of the present disclosure provides a spiro compound represented by Formula 1 below.

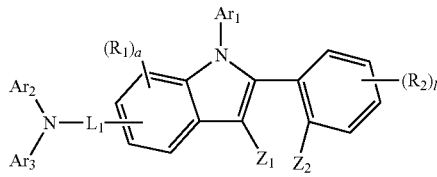

Formula 1

In Formula 1, $R_1$ and $R_2$ may be each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, or combined with an adjacent group to form a ring.

In Formula 1, $Ar_1$ may be a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms.

In an embodiment, in the substituted or unsubstituted $Ar_1$, there may be one to eight substituents, and in case of two or more substituents, the substituents may be the same or different.

In an embodiment, in case of one of more substituents of $Ar_1$, the substituent of $Ar_1$ may be a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms.

In Formula 1, $Ar_2$ and $Ar_3$ may be each independently a substituted or unsubstituted aryl group of 6 to 30 ring-forming carbon atoms, or a substituted or unsubstituted heteroaryl group of 2 to 30 ring-forming carbon atoms.

In Formula 1, $L_1$ may be a direct linkage, a substituted or unsubstituted arylene group of 6 to 30 ring-forming carbon atoms, or a substituted or unsubstituted heteroarylene group of 2 to 30 ring-forming carbon atoms.

In an embodiment, $L_1$ may be a direct linkage.

In Formula 1, a is an integer of 0 to 3, and l is an integer of 0 to 4. Meanwhile, if a is 2 or more, multiple $R_1$ groups are the same or different, and if l is 2 or more, multiple $R_2$ groups are the same or different.

In Formula 1, $Z_1$ and $Z_2$ form spiro bonds with a ring compound represented by Formula 2 below. For example, $Z_1$ and $Z_2$ may both be bonded to the same spiro atom or spiro center.

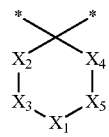

Formula 2

In Formula 2, $X_1$ may be a direct linkage, O, S, $CR_5R_6$, $SiR_7R_8$, $BR_9$, or $NR_{10}$.

In Formula 2, $X_2$ to $X_5$ may be each independently $CR_{11}R_{12}$.

In Formula 2, $R_5$ to $R_{12}$ may be each independently a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, and * indicates a binding site to an adjacent atom of Formula 1.

With respect to the spiro compound of an embodiment, represented by Formula 1, the same explanation on the spiro compound in the organic electroluminescence device of an embodiment will be applied.

The spiro compound according to an embodiment may be any one selected among the compounds represented in Compound Group 1.

Hereinafter, the subject matter of the present disclosure will be more particularly explained referring to embodiments and comparative embodiments. The following embodiments are only illustrations to assist the understanding of the present disclosure, and the scope of the present disclosure is not limited thereto.

EXAMPLES

1. Synthesis of Spiro Compound (1) Synthetic Example 1—Synthesis of Compound 5

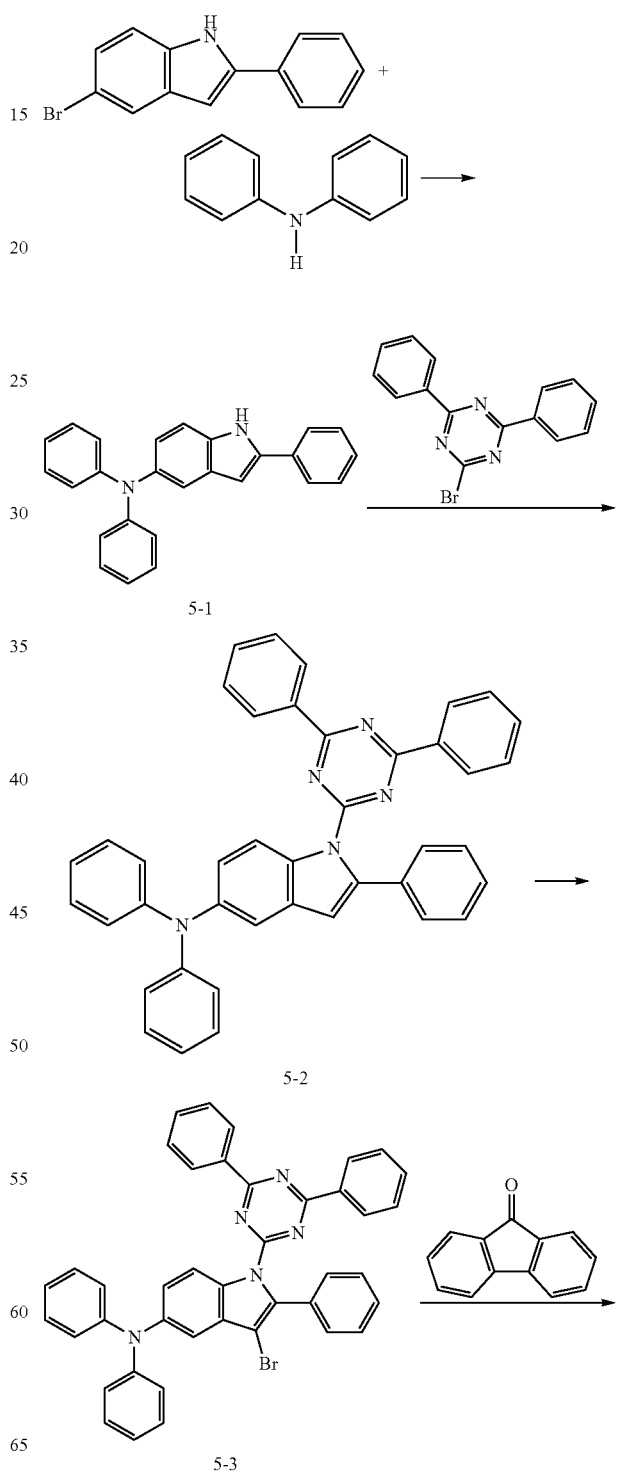

-continued

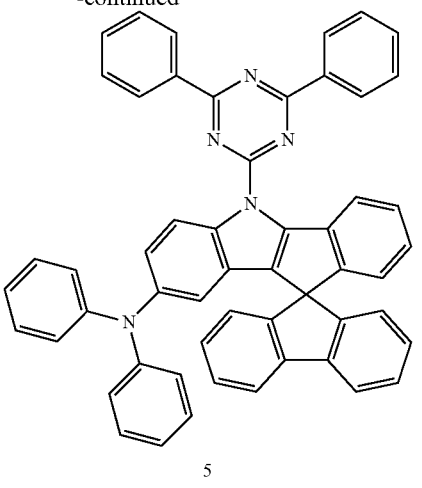

5

1) Synthesis of Intermediate 5-1

Under a nitrogen atmosphere, 10 g (36 mmol) of 5-bromo-2-phenyl-1H-indole, 12 g (72 mmol) of diphenylamine, 1.8 g (1.5 mmol) of tetrakis(triphenylphosphine) palladium, 15 g (108 mmol) of potassium carbonate, 50 ml of 1,4-dioxane, 50 ml of toluene, and 20 ml of distilled water were added to a reactor, and stirred at 120° C. for 12 hours. After finishing the reaction, extraction was performed using ethyl acetate and distilled water. An organic layer was concentrated under a reduced pressure and then, separated by column chromatography to obtain 4.4 g (yield 34%) of Intermediate 5-1.

2) Synthesis of Intermediate 5-2

4 g (11 mmol) of a compound represented by Intermediate 5-1, 4.7 g (15 mmol) of 2-bromo-4,6-diphenyl-1,3,5-triazine, 0.2 g (0.3 mmol) of tris(dibenzylidenacetone) dipalladium, 0.3 g (1 mmol) of tri tertiary butyl phosphonium tetrafluoroborate, 2 g (20 mmol) of sodium tert-butoxide and 20 ml of xylene were added and refluxed for 12 hours. After finishing the reaction, filtration was performed in a hot state under a reduced pressure. After drying the solution under a reduced pressure, column chromatography was performed to obtain 3.4 g (yield 53%) of Intermediate 5-2.

3) Synthesis of Intermediate 5-3

To a reactor, 3.4 g (5.8 mmol) of Intermediate 5-2, and 100 ml of methylene chloride were added and then, cooled to 0° C. 50 ml of a solution in which bromine was dissolved in methylene chloride was added thereto dropwisely, and the temperature was elevated to room temperature and then, stirring was performed for 2 hours. An aqueous sodium bicarbonate solution was added thereto, an organic layer was extracted and concentrated under a reduced pressure, and separation by column chromatography was performed to obtain 3.2 g (yield 82%) of Intermediate 5-3.

4) Synthesis of Compound 5

3.2 g (4.8 mmol) of Intermediate 5-3, and 30 ml of tetrahydrofuran were added and then, cooled to −78° C. 4 ml (6 mmol) of butyllithium (1.6 M hexane solution) was added thereto dropwisely. After stirring at −78° C. for 2 hours, 1.1 g (6 mmol) of 9-fluorenone was dissolved in 10 ml of tetrahydrofuran, and this solution was added dropwisely, followed by elevating the temperature to room temperature and stirring for 2 hours. Water was added, and an organic layer was extracted using ethyl acetate, and then, separated using column chromatography to obtain 2.7 g (molecular weight 753, 75%) of Compound 5.

(2) Synthetic Example 2—Synthesis of Compound 13

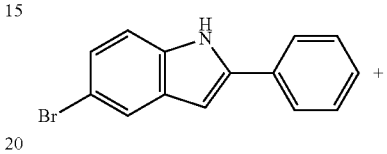

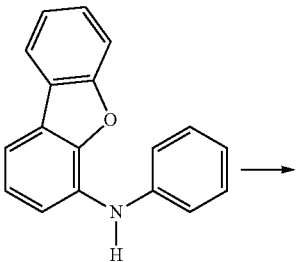

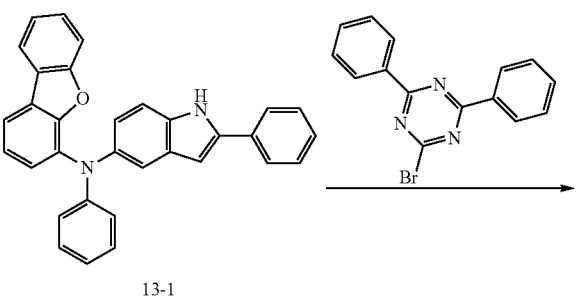

13-1

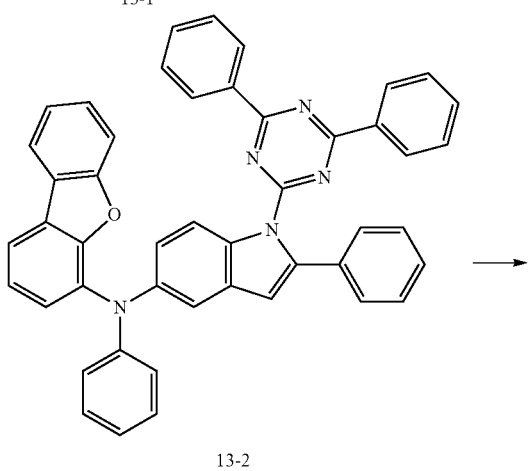

13-2

51
-continued
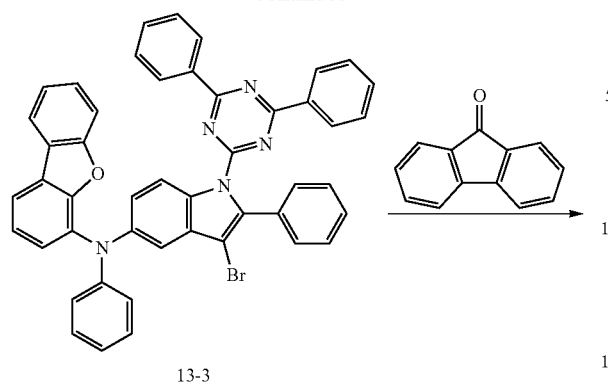
13-3
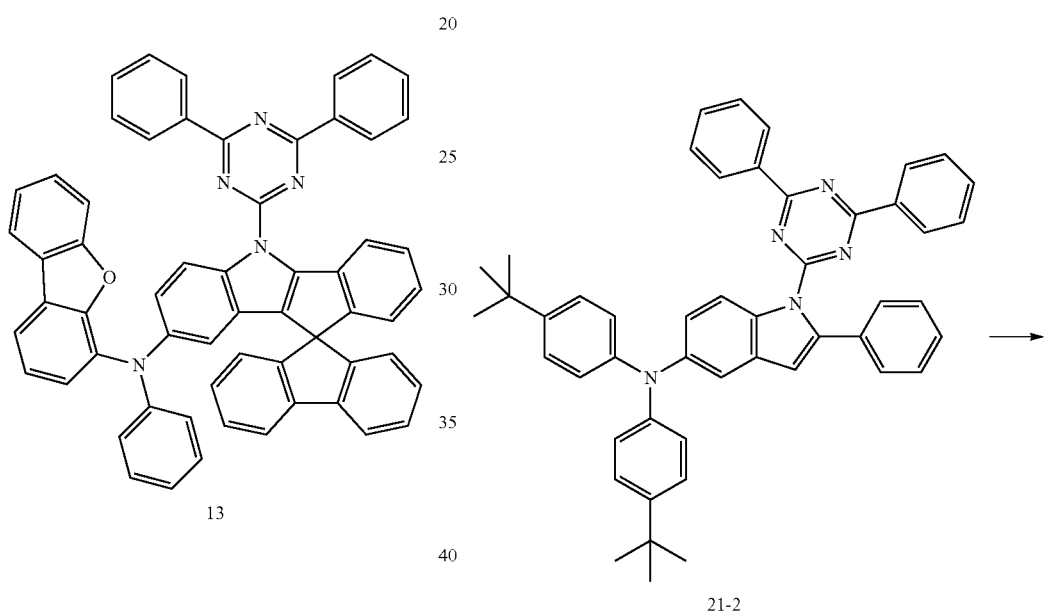
13
Compound 13 (molecular weight 843) was synthesized by substantially the same method and process as those of Compound 5, except for changing diphenylamine into N-phenyldibenzo[b,d]furan-4-amine in the reaction.
(3) Synthetic Example 3—Synthesis of Compound 21
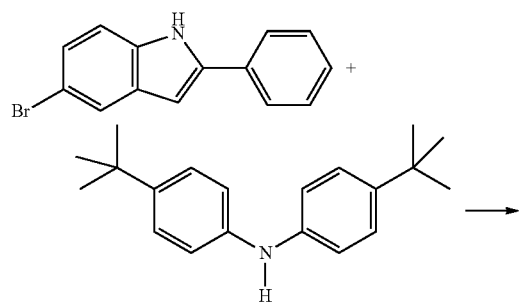
52
-continued
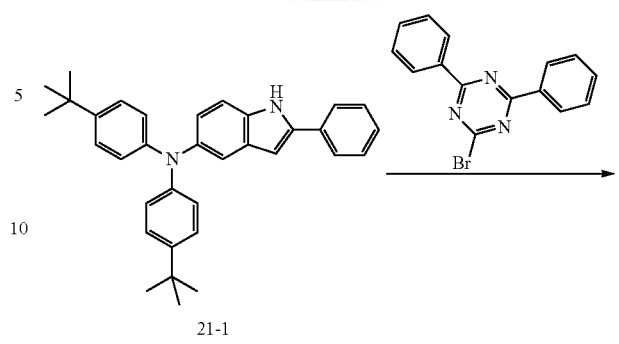
21-1
21-2
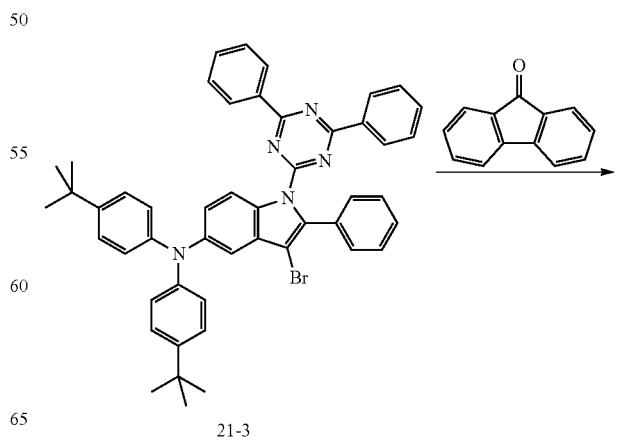
21-3

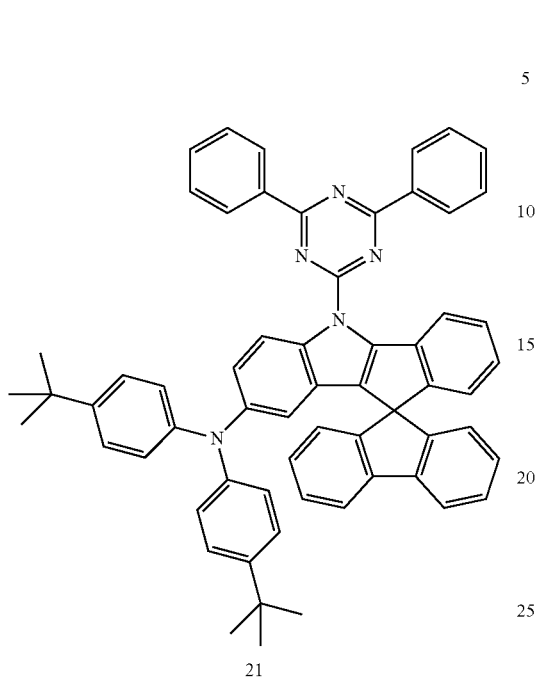

21

Compound 21 (molecular weight 865) was synthesized by substantially the same method and process as those of Compound 5, except for changing diphenylamine into bis (4-(tert-butyl)phenyl)amine in the reaction.

2. Calculation of Energy Level of Spiro Compound (Manufacture of Organic Electroluminescence Device)

TABLE 1

| Example Compound |
|---|
| 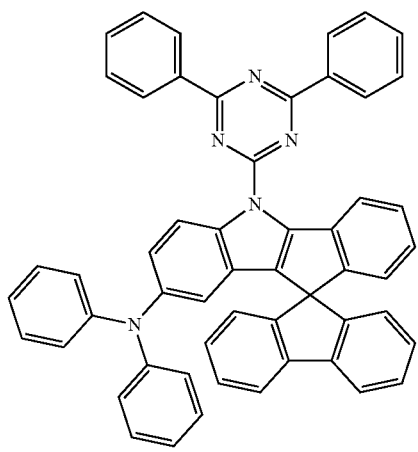<br>5 |

TABLE 1-continued

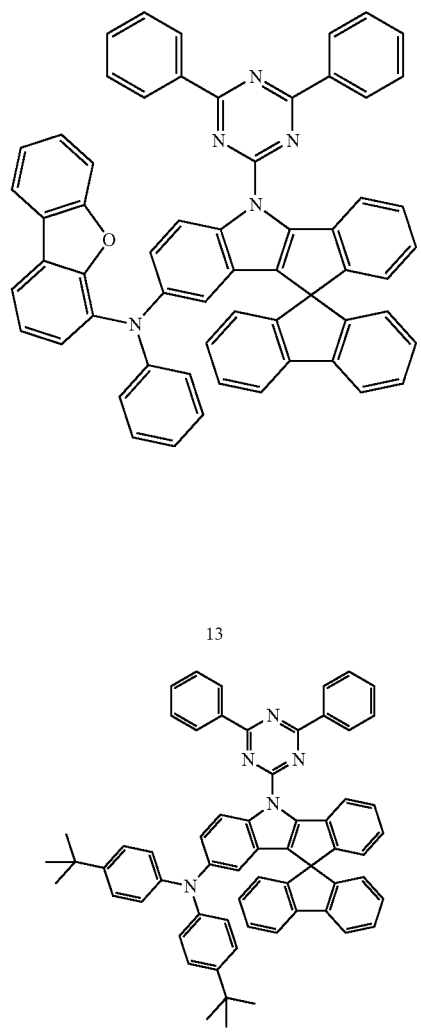

| Comparative Compound |
|---|
| 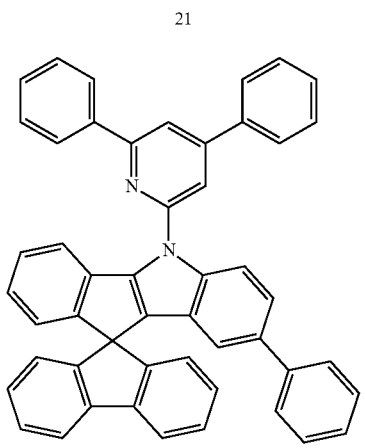<br>Ref. 1 |

TABLE 1-continued

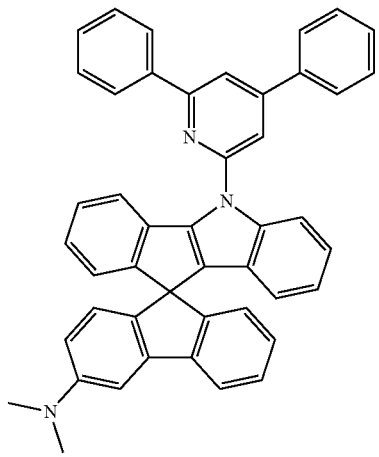 [SMILES: CN(C)c1ccc2c(c1)-c1ccccc1C21c2ccccc2-c2c1c1ccccc1n2-c1cc(-c2ccccc2)cc(-c2ccccc2)n1]

Ref. 2

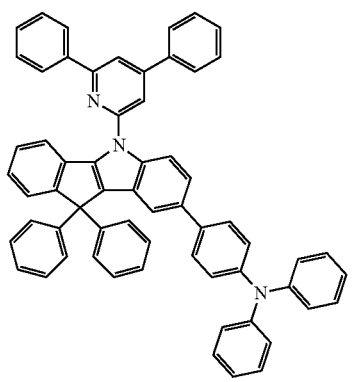 [SMILES: c1ccc(-c2cc(-c3ccccc3)nc(-n3c4c(c5cc(-c6ccc(N(c7ccccc7)c7ccccc7)cc6)ccc53)C(c3ccccc3)(c3ccccc3)c3ccccc3-4)c2)cc1]

Ref. 3

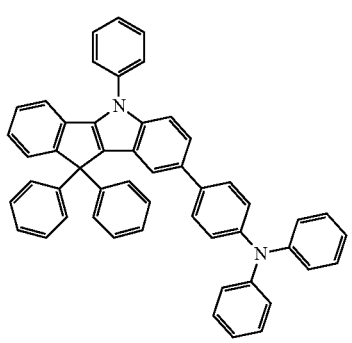 [SMILES: c1ccc(N(c2ccccc2)c2ccc(-c3ccc4c(c3)c3c(n4-c4ccccc4)-c4ccccc4C3(c3ccccc3)c3ccccc3)cc2)cc1]

Ref. 4

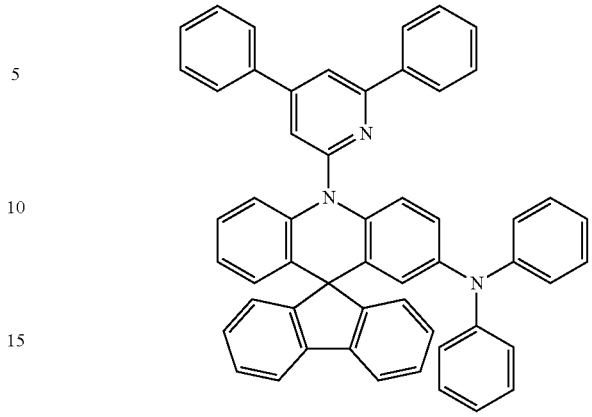

Ref. 5

The S1 level and T1 level of the Example Compounds and Comparative Compounds were calculated by a non-empirical molecular orbital method. Particularly, using Gaussian09 of Gaussian Co., calculation was conducted using a functional of B3LYP and a basis function of 6-31G*. The results are shown in Table 1 below. ΔEst means a difference between a singlet energy level and a triplet energy level.

TABLE 2

| | S1 energy level (eV) | T1 energy level (eV) | $\Delta E_{ST}$ |
|---|---|---|---|
| Example Compound 5 | 2.418 | 2.373 | 0.045 |
| Example Compound 13 | 2.424 | 2.378 | 0.046 |
| Example Compound 21 | 2.326 | 2.311 | 0.015 |
| Comparative Compound Ref 1 | 2.919 | 2.508 | 0.411 |
| Comparative Compound Ref 2 | 2.867 | 2.497 | 0.370 |
| Comparative Compound Ref 3 | 2.937 | 2.502 | 0.435 |
| Comparative Compound Ref 4 | 3.428 | 2.532 | 0.896 |
| Comparative Compound Ref 5 | 2.424 | 2.404 | 0.020 |

Referring to the results of Table 2 above, all the Example Compounds show small ΔEst values, and seem to be suitably used as materials for thermally activated delayed fluorescence, but the Comparative Compounds show relatively large ΔEst values of 0.2 eV or more, and are unsuitable as materials for thermally activated delayed fluorescence.

3. Manufacture and Evaluation of Organic Electroluminescence Device Including Spiro Compound (Manufacture of Organic Electroluminescence Device)

An organic electroluminescence device of an embodiment, including the spiro compound of an embodiment in an emission layer was manufactured by a method below. For example, a case where the emission layer of an organic electroluminescence device of an embodiment includes the spiro compound of an embodiment as a TADF dopant will be explained as an embodiment.

Organic electroluminescence devices of Example 1 to Example 3 were manufactured using the organic compound of the above-explained Spiro Compounds 5, 13 and 21 as materials for an emission layer, and organic electroluminescence devices of Comparative Example 1 to Comparative Example 5 were manufactured using Comparative Compound ref 1 to Comparative Compound ref 5 in Table 1 as materials for an emission layer.

As an anode, an ITO glass substrate of 15 Ω/cm² (1200 Å) of Corning Co. as cut into a size of 50 mm×50 mm×0.7 mm, washed using isopropyl alcohol and pure water for 5 minutes, respectively, and then washed with ultrasonic waves, exposed to UV for 30 minutes and exposed to ozone. Then, this glass substrate was installed in a vacuum deposition apparatus.

On the ITO anode, Compound HT3 was vacuum deposited to deposit a hole transport layer with a thickness of 70 nm, and TCTA was deposited to a thickness of 10 nm to form a hole transport region.

Then, for forming an emission layer, the spiro compound of an embodiment or the Comparative Compound and mCBP were co-deposited as a host in a weight ratio of 20% to form a layer with a thickness of 300 Å. On the emission layer, a layer with a thickness of 300 Å was formed using TPBi, and a layer with a thickness of 5 Å was formed using Liq to form an electron transport region. Then, a second electrode with a thickness of 1000 Å was formed using aluminum (Al).

In the Examples, the hole transport region, the emission layer, the electron transport region, and the second electrode were formed using a vacuum deposition apparatus.

The efficiency and life of the organic electroluminescence devices according to Examples 1 to 3 and Comparative Examples 1 to 5 were measured and shown in Table 3 below. For the evaluation of the light-emitting properties of the organic electroluminescence devices thus manufactured, a 09920-11 light distribution measurement system of Hamamatsu Photonics Co. was used.

(Evaluation of Properties of Organic Electroluminescence Device)

TABLE 3

| | Dopant | Color | Efficiency | Life |
|---|---|---|---|---|
| Comparative Example 1 | Ref. 1 | Sky blue | 100% | 100% |
| Comparative Example 2 | Ref. 2 | Sky blue | 75% | 60% |
| Comparative Example 3 | Ref. 3 | Sky blue | 113% | 97% |
| Comparative Example 4 | Ref. 4 | Blue | 60% | 85% |
| Comparative Example 5 | Ref. 5 | Green | 170% | 122% |
| Example 1 | Compound 5 | Green | 210% | 135% |
| Example 2 | Compound 13 | Green | 231% | 158% |
| Example 3 | Compound 21 | Green | 227% | 140% |

Referring to Table 3 above, Comparative Examples 1 to 4 are unsuitable for emitting green light. In addition, it is confirmed that Comparative Examples 1 to 5 show lower device efficiency and shorter life when compared with Examples 1 to 3. Examples 1 to 3, in which an indenoindole derivative essentially includes an aryl amine group combined with a core structure, are suitable as materials for thermally activated delayed fluorescence emitting green light, and accordingly, are confirmed to contribute to the high efficiency and long life of a device.

Although embodiments of the present disclosure have been described, it could be understood that a skilled person in corresponding technical field or a person having an ordinary knowledge in corresponding technical field could diversely change and modify the subject matter of the present disclosure within the scope and technical area of the present disclosure as hereinafter claimed.

Accordingly, the technical scope of the present disclosure should not be limited to the description in the detailed description of the specification, but should instead be determined by the appended claims, and equivalents thereof.

In an organic electroluminescence device emitting green light, high efficiency and long life are required. Accordingly, embodiments of the present disclosure relating to an organic electroluminescence device and a spiro compound has high industrial applicability.

The invention claimed is:

1. An organic electroluminescence device, comprising:
a first electrode;
a hole transport region on the first electrode;
an emission layer on the hole transport region;
an electron transport region on the emission layer; and
a second electrode on the electron transport region,
wherein the emission layer comprises a spiro compound containing an aryl amine group and an indenoindole derivative and the emission layer emits green light,
wherein the emission layer comprises a host and a dopant, and the dopant comprises the spiro compound.

2. The organic electroluminescence device according to claim 1, wherein, in the spiro compound, the indenoindole derivative and a pentagonal or hexagonal ring of the spiro compound form a spiro bond.

3. The organic electroluminescence device according to claim 1, wherein the indenoindole derivative and the aryl amine group are bonded via a linker or via a direct linkage.

4. The organic electroluminescence device according to claim 1, wherein the emission layer is a thermally activated delayed fluorescence emission layer.

5. An organic electroluminescence device, comprising:
a first electrode;
a hole transport region on the first electrode;
an emission layer on the hole transport region;
an electron transport region on the emission layer; and
a second electrode on the electron transport region,
wherein the emission layer comprises a spiro compound containing an aryl amine group and an indenoindole derivative and the emission layer emits green light, and
wherein the spiro compound has an absolute value of a difference between a singlet energy level and a triplet energy level of 0.2 eV or less.

6. An organic electroluminescence device, comprising:
a first electrode;
a hole transport region on the first electrode;
an emission layer on the hole transport region;
an electron transport region on the emission layer; and
a second electrode on the electron transport region,
wherein the emission layer comprises a spiro compound containing an aryl amine group and an indenoindole derivative and the emission layer emits green light, and
wherein the spiro compound is represented by the following Formula 1:

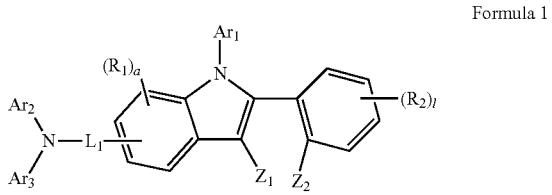

Formula 1 in Formula 1,
- $R_1$ and $R_2$ are each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, or combined with an adjacent group to form a ring,
- $Ar_1$ is a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms,
- $Ar_2$ and $Ar_3$ are each independently a substituted or unsubstituted aryl group of 6 to 30 ring-forming carbon atoms, or a substituted or unsubstituted heteroaryl group of 2 to 30 ring-forming carbon atoms,
- $L_1$ is a direct linkage, a substituted or unsubstituted arylene group of 6 to 30 ring-forming carbon atoms, or a substituted or unsubstituted heteroarylene group of 2 to 30 ring-forming carbon atoms,
- a is an integer of 0 to 3,
- l is an integer of 0 to 4, and
- $Z_1$ and $Z_2$ form spiro bonds of a ring compound represented by the following Formula 2:

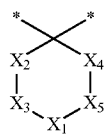

Formula 2 in Formula 2,
- $X_1$ is a direct linkage, O, S, $CR_5R_6$, $SiR_7R_8$, $BR_9$, or $NR_{10}$,
- $X_2$ to $X_5$ are each independently $CR_{11}R_{12}$,
- $R_5$ to $R_{12}$ are each independently a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, and
- * indicates a binding site to an adjacent atom of Formula 1.

7. The organic electroluminescence device according to claim 6, wherein Formula 2 is represented by any one selected from among the following Formula 2-1 to Formula 2-7:

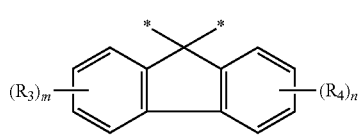

Formula 2-1

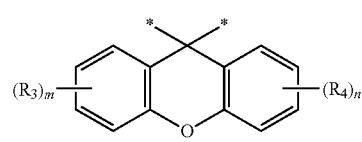

Formula 2-2

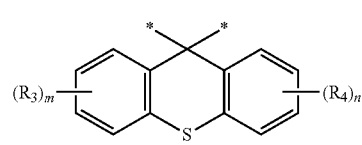

Formula 2-3

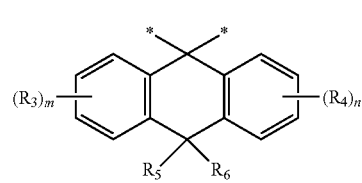

Formula 2-4

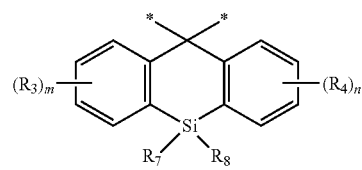

Formula 2-5

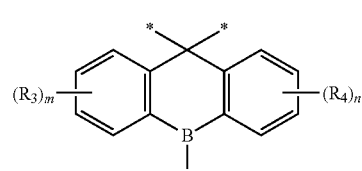

Formula 2-6

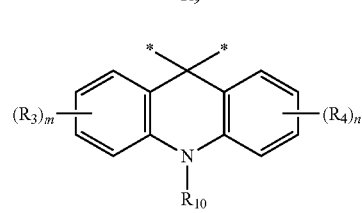

Formula 2-7 in Formula 2-1 to Formula 2-7,
- $R_3$ and $R_4$ are each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, or combined with an adjacent group to form a ring,
- m and n are each independently an integer of 0 to 4,
- $R_5$ to $R_{10}$ are the same as defined in Formula 2, and
- * indicates a binding site to an adjacent atom of Formula 1.

8. The organic electroluminescence device according to claim 6, wherein Formula 1 is represented by the following Formula 3:

Formula 3

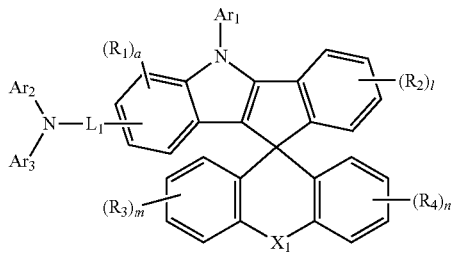

in Formula 3,

R$_3$ and R$_4$ are each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, a substituted or unsubstituted heteroaryl group of 2 to 30 ring-forming carbon atoms, a substituted or unsubstituted cycloalkyl group of 6 to 30 ring-forming carbon atoms, or a substituted or unsubstituted heterocycloalkyl group of 2 to 30 ring-forming carbon atoms, or combined with an adjacent group to form a ring, m and n are each independently an integer of 0 to 4, and R$_1$, R$_2$, R$_5$ to R$_{10}$, Ar$_1$ to Ar$_3$, L$_1$, X$_1$, a, and l are the same as defined in Formula 1 and Formula 2.

9. The organic electroluminescence device according to claim 6, wherein Ar$_1$ is a substituted or unsubstituted phenyl group, a substituted or unsubstituted pyridyl group, a substituted or unsubstituted pyrimidyl group, or a substituted or unsubstituted triazinyl group.

10. The organic electroluminescence device according to claim 6, wherein L$_1$ is a direct linkage.

11. The organic electroluminescence device according to claim 8, wherein Formula 3 is represented by any one selected from among the following Formula 3-1 to Formula 3-5:

Formula 3-1

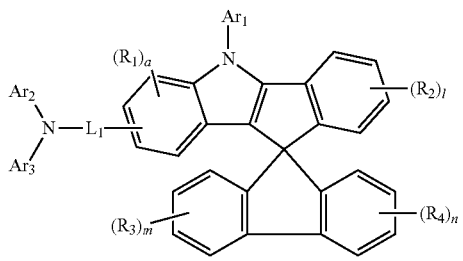

Formula 3-2

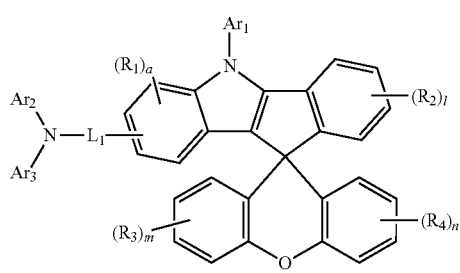

Formula 3-3

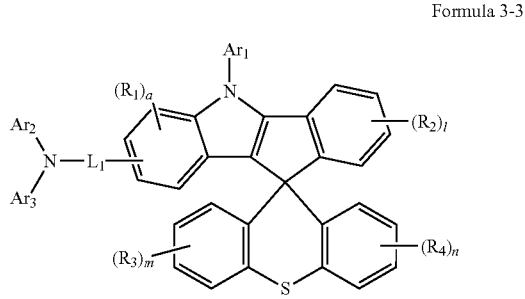

Formula 3-4

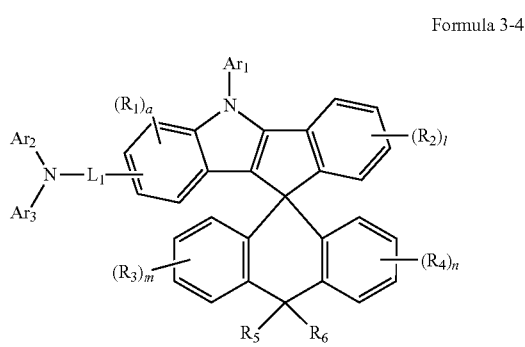

Formula 3-5

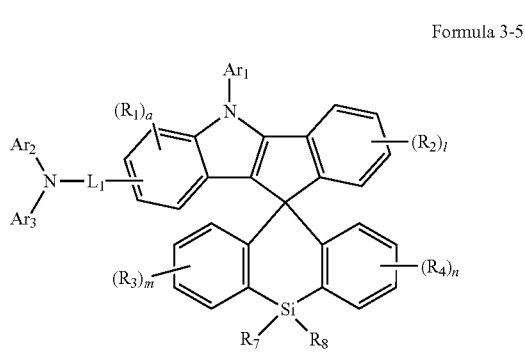

in Formulae 3-1 to 3-5,

R$_1$ to R$_8$, Ar$_1$ to Ar$_3$, L$_1$, a, and l to n are the same as defined in Formula 3.

12. The organic electroluminescence device according to claim 6, wherein the spiro compound represented by Formula 1 is any one selected from among compounds represented in the following Compound Group 1:
Compound Group 1
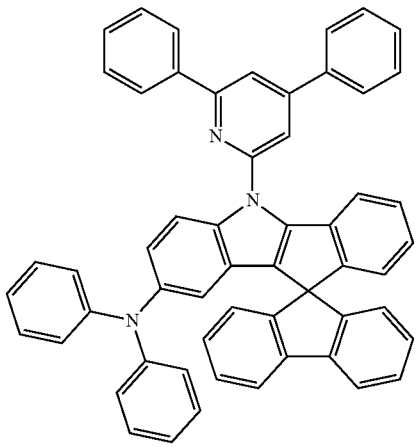
1
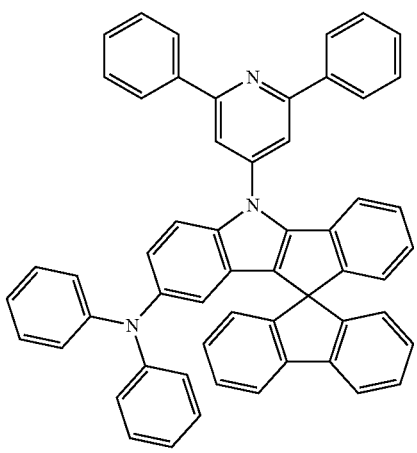
2
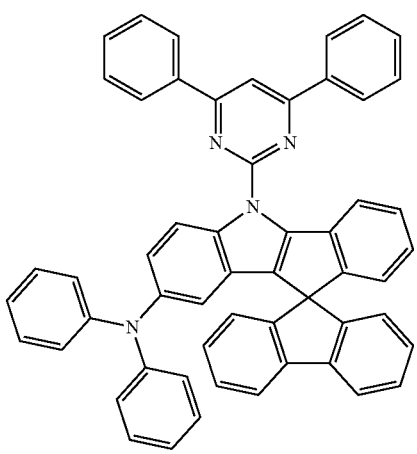
3
-continued
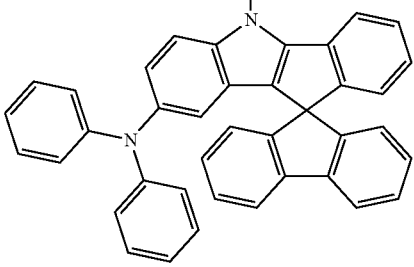
4
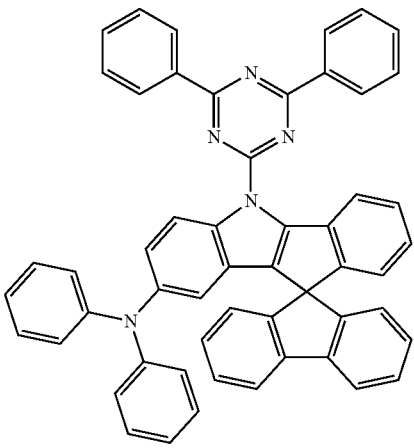
5
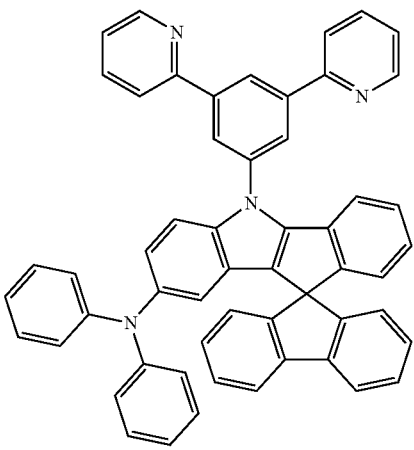
6

65
-continued
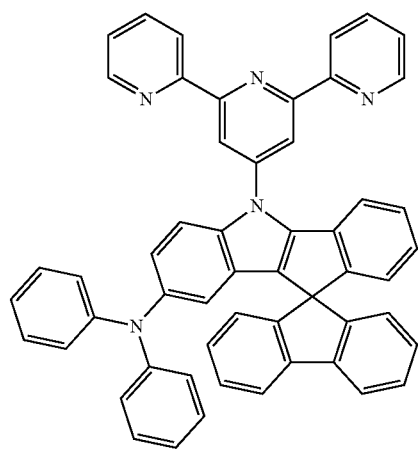
7
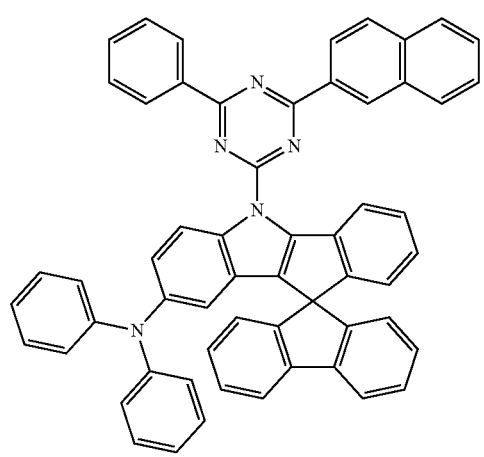
8
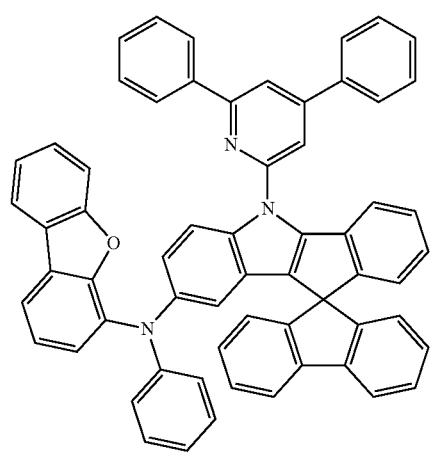
9
66
-continued
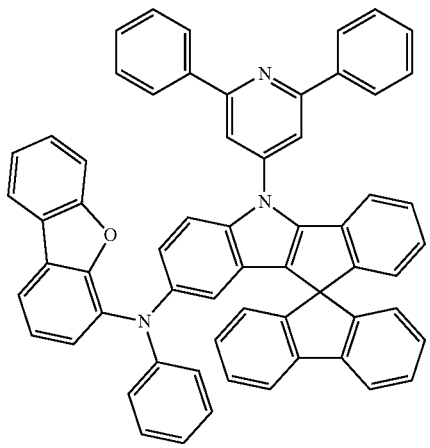
10
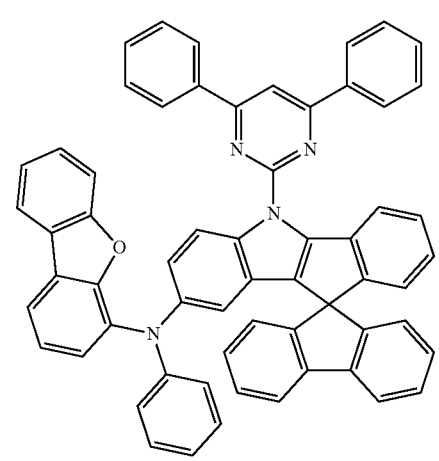
11
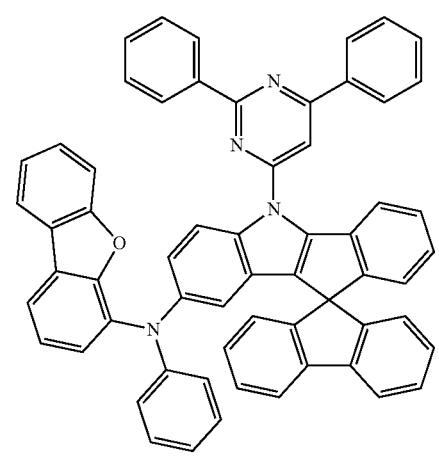
12

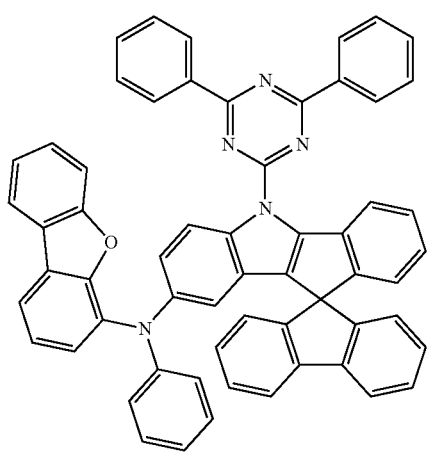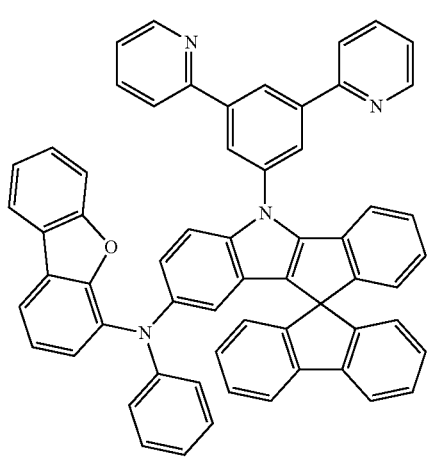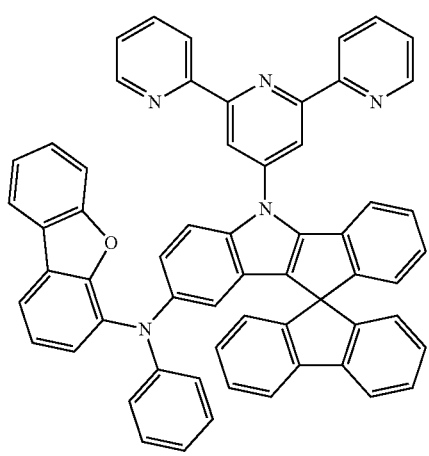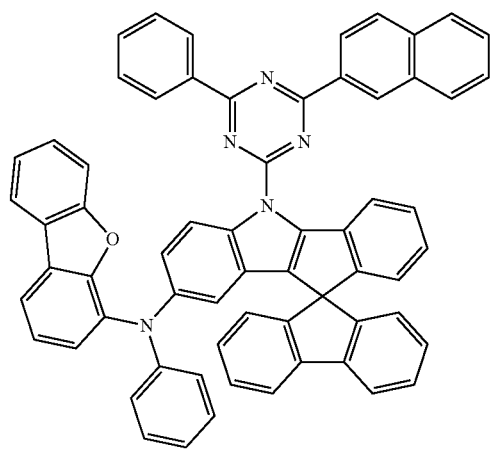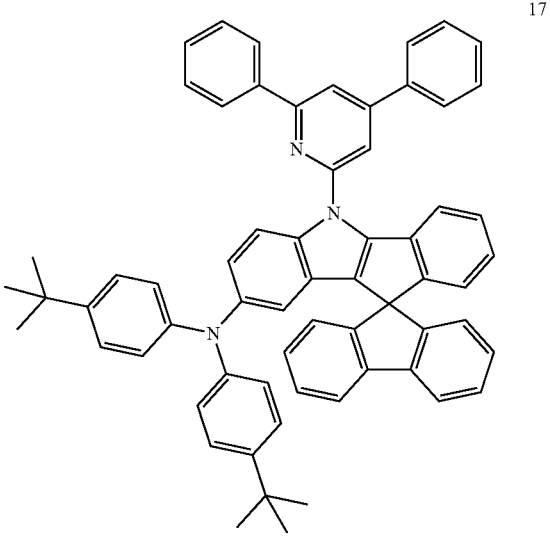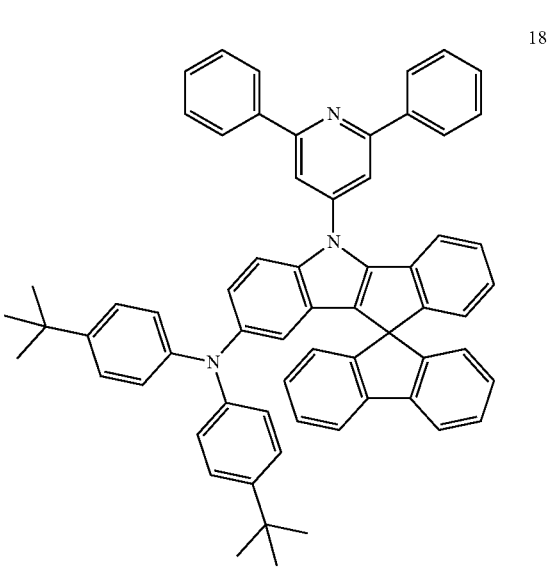

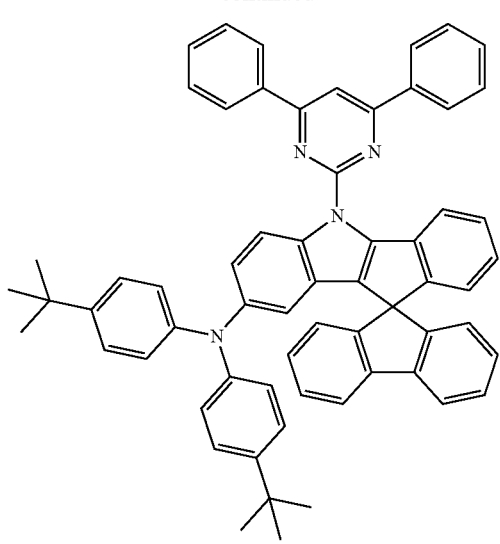
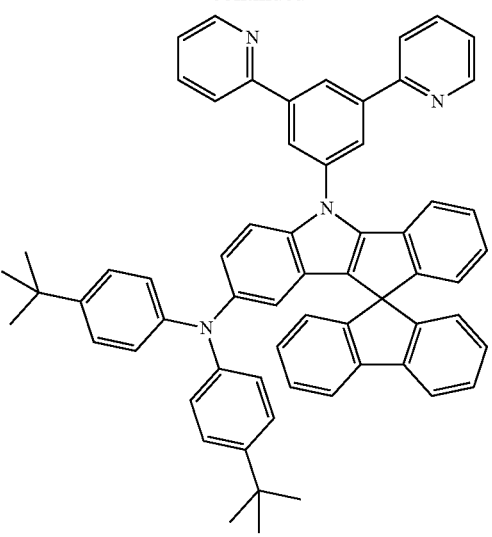

-continued
25
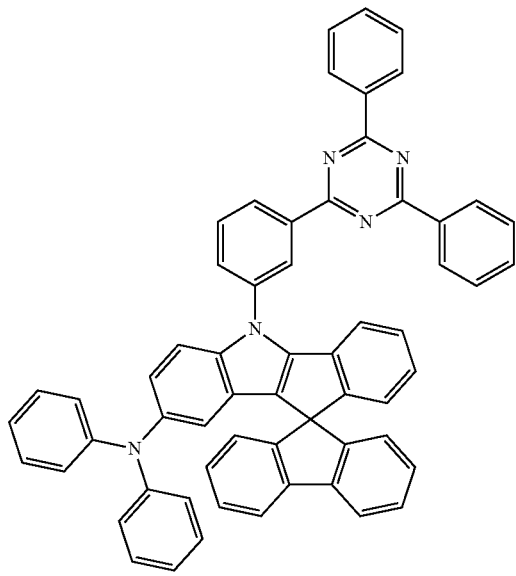
26
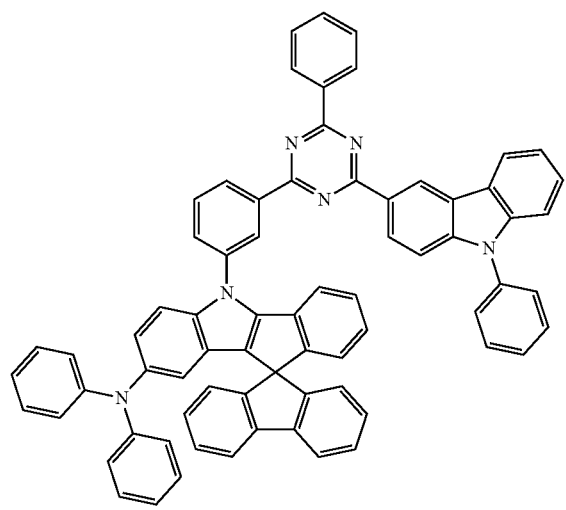
27
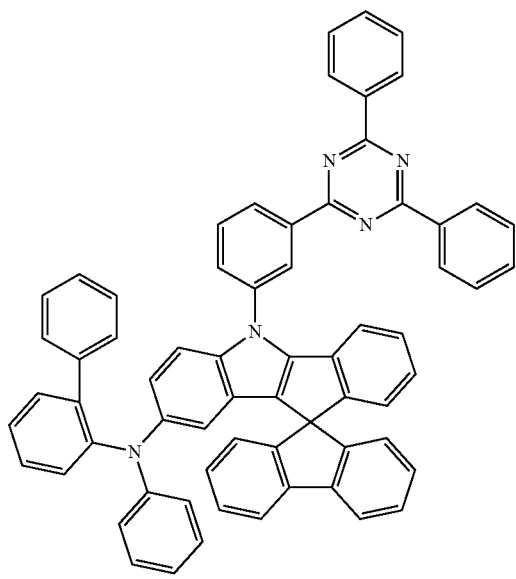
-continued
28
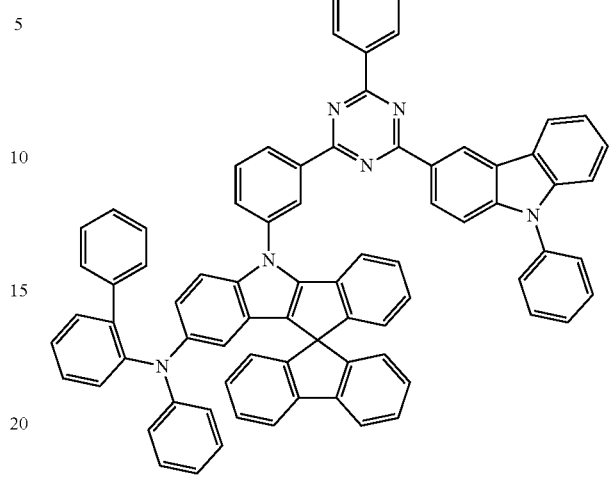
29
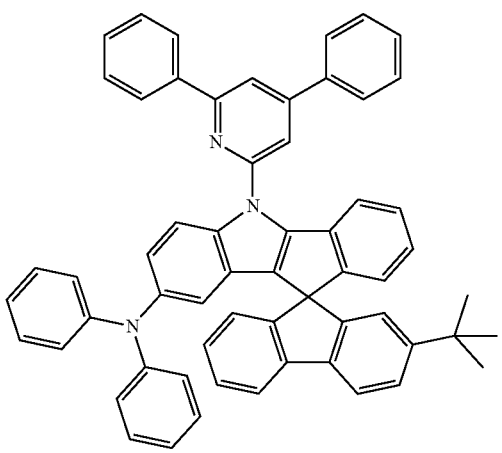
30
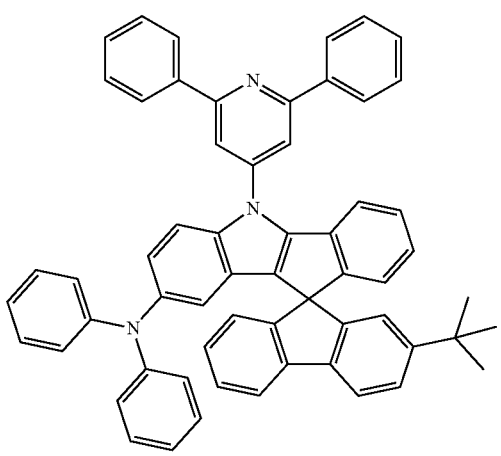

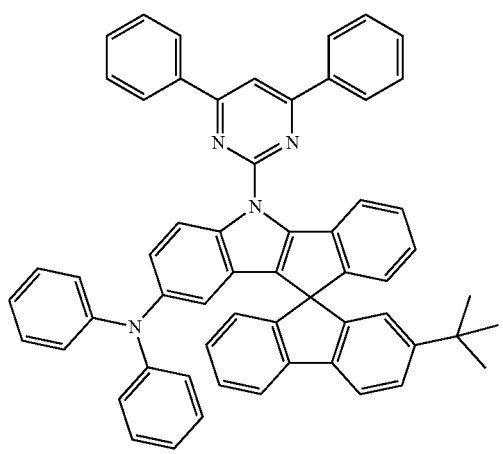
31
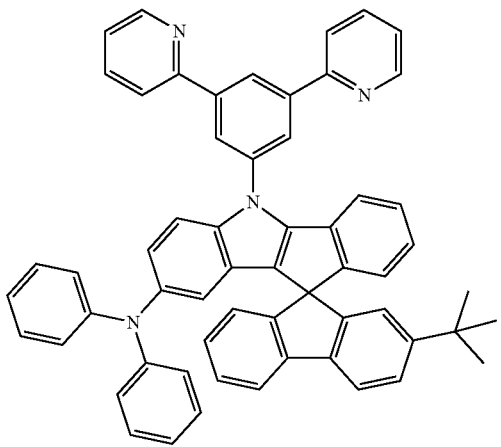
34
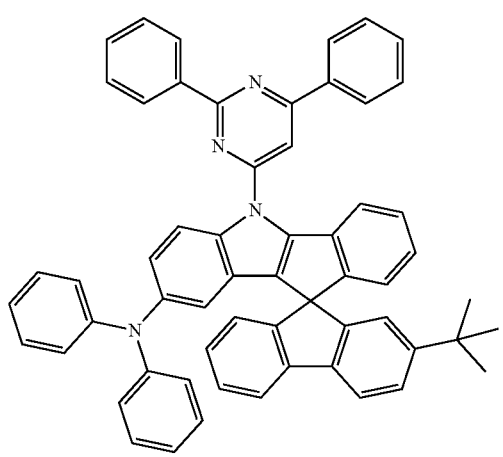
32
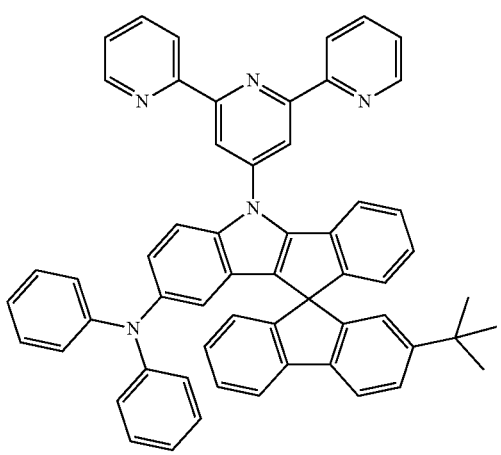
35
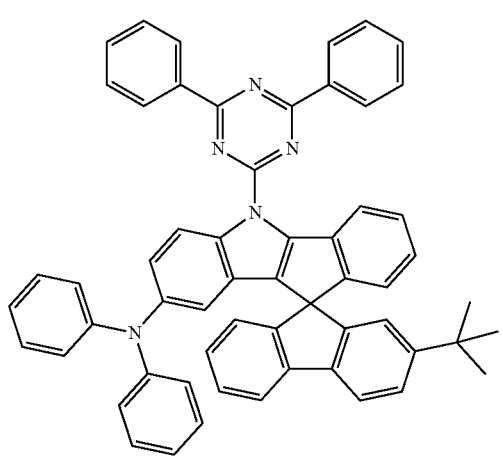
33
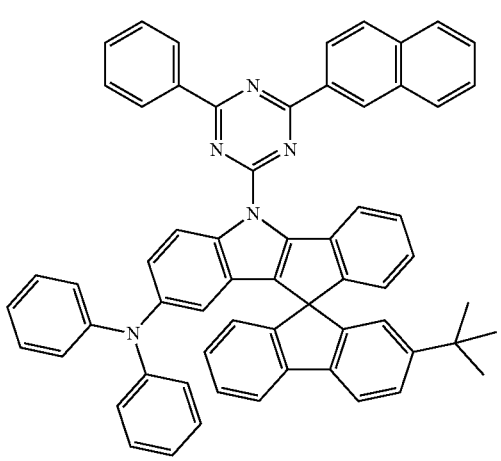
36

37
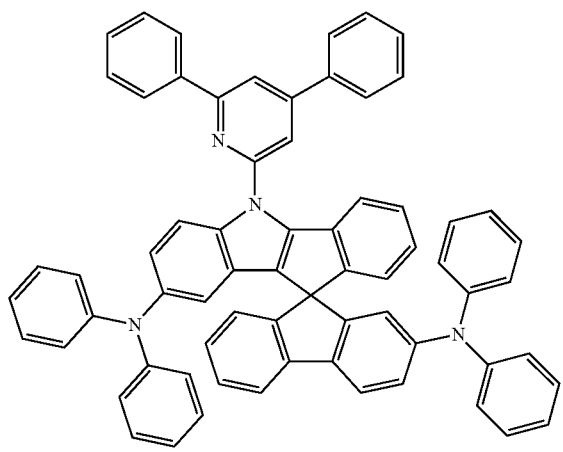
38
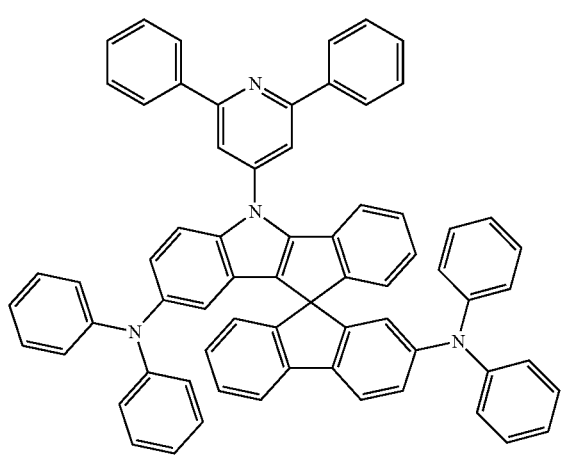
39
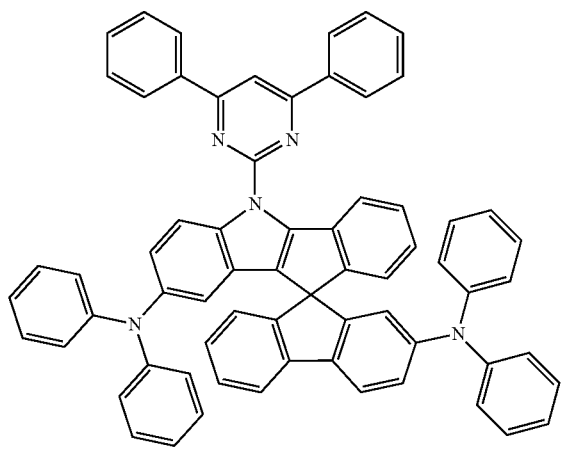
40
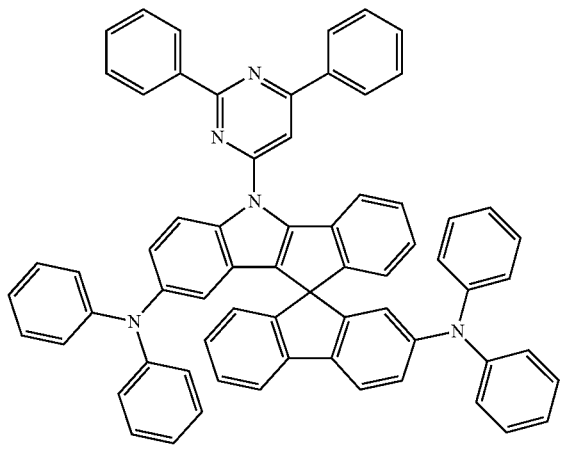
41
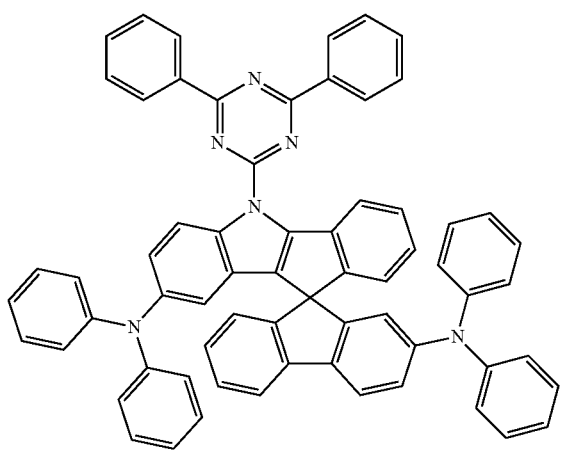
42
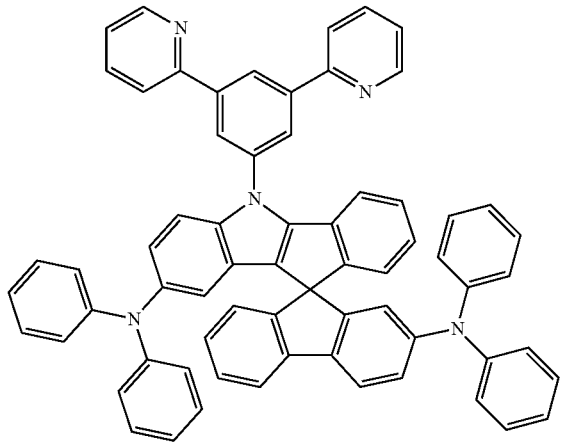

-continued
43
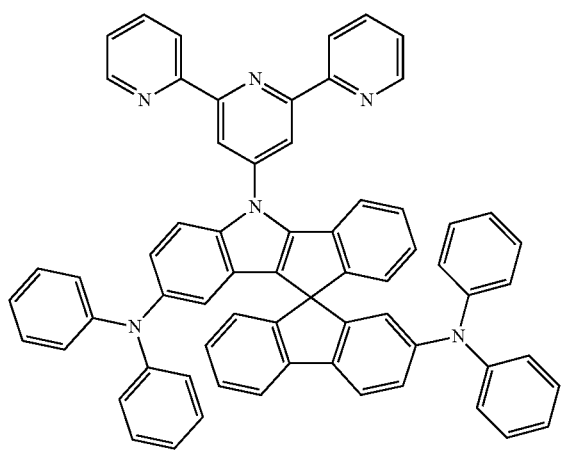
44
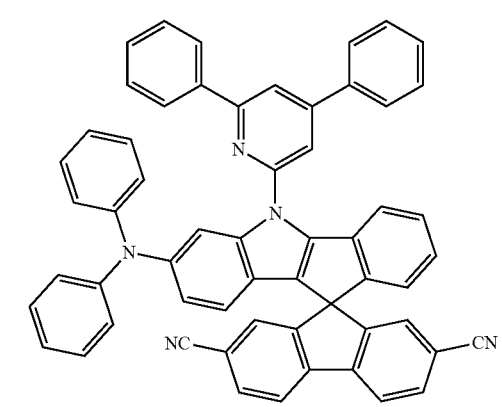
45
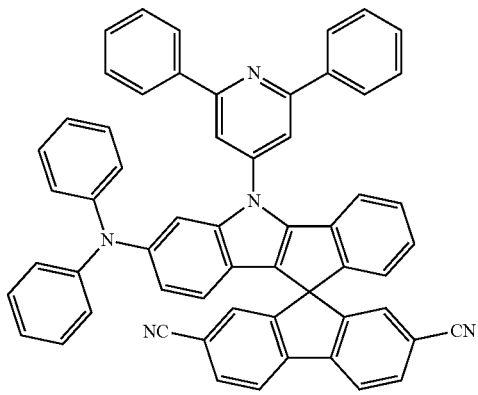
-continued
46
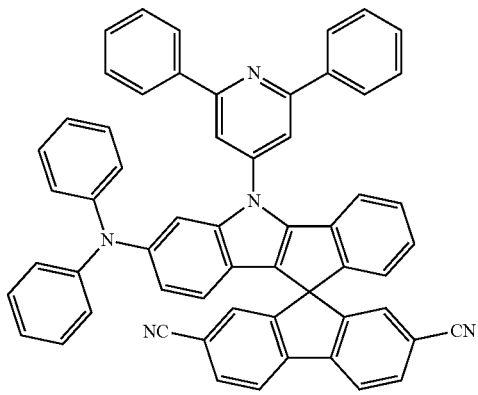
47
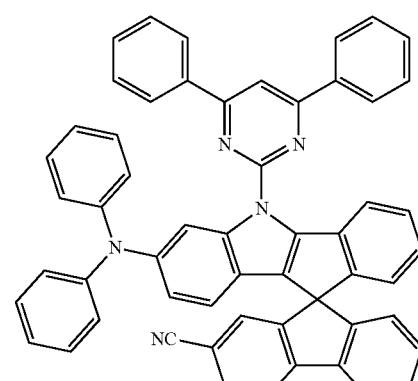
48
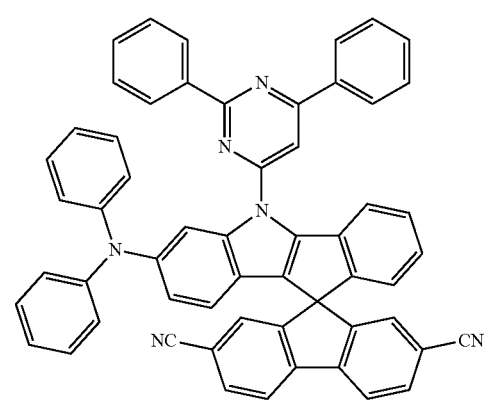
49
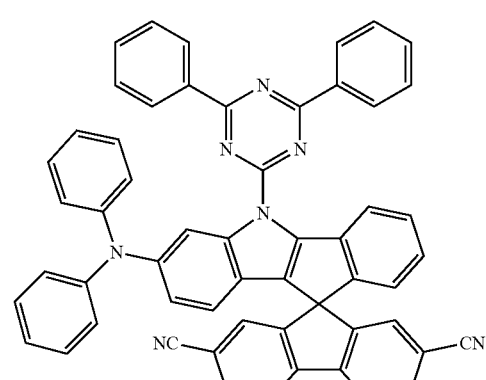

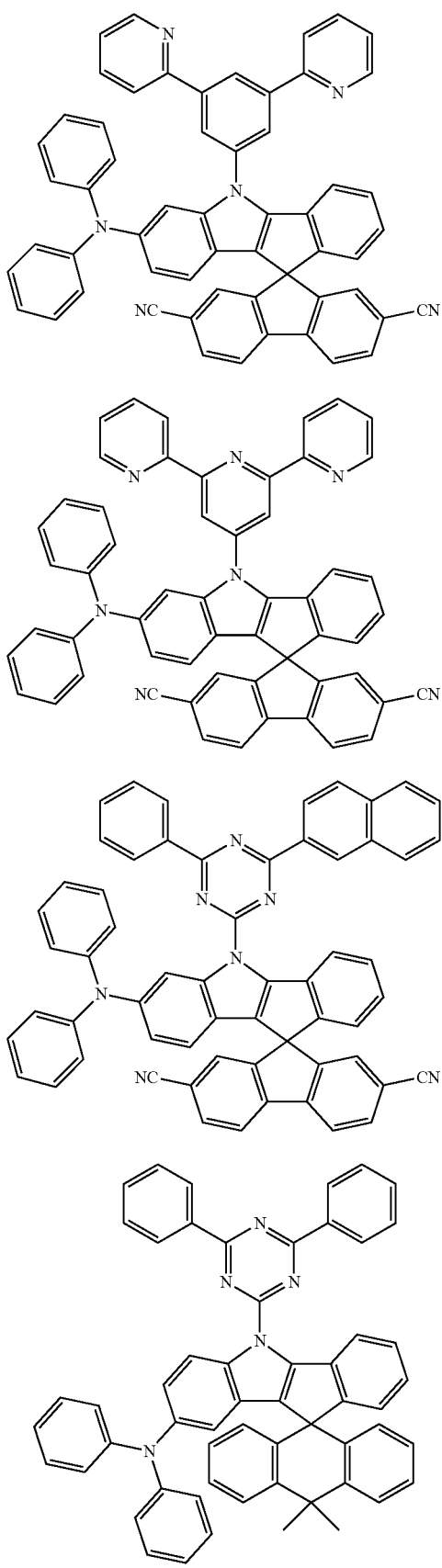
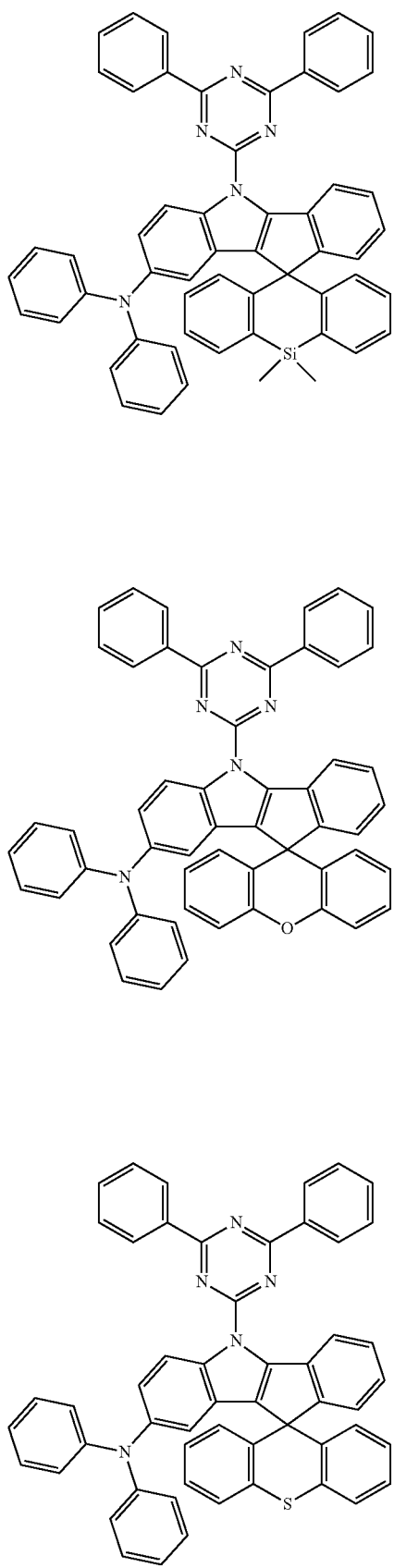

81
-continued
57
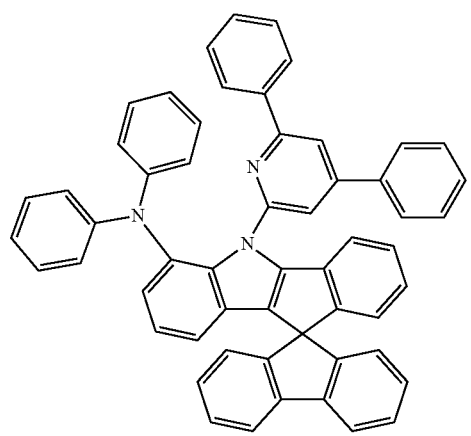
58
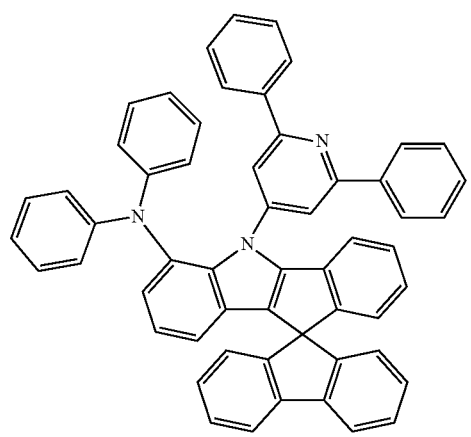
59
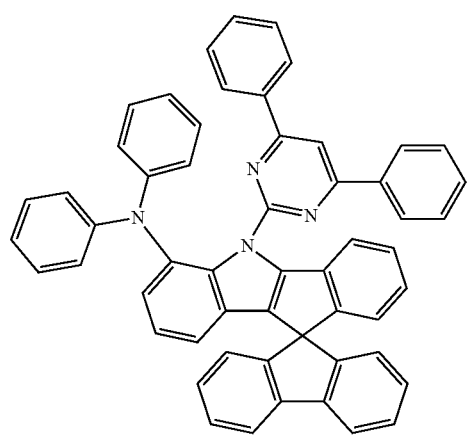
82
-continued
60
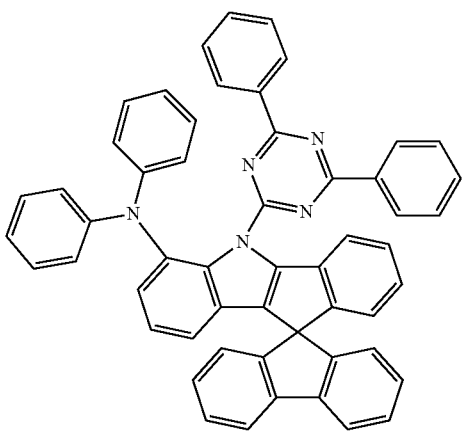
61
62

83
-continued
63
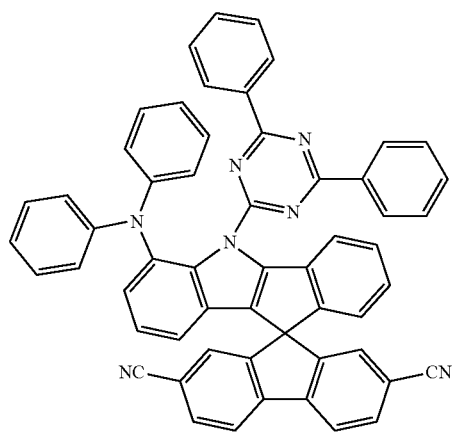
64
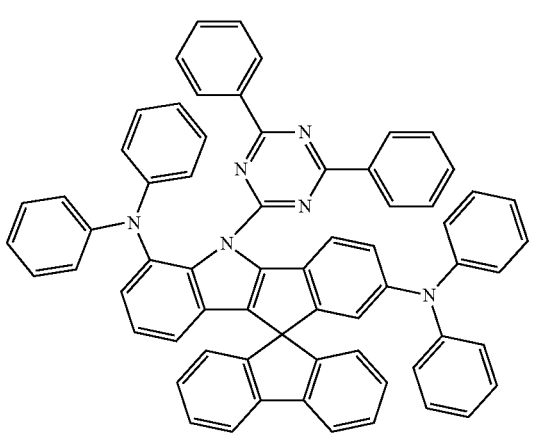
65
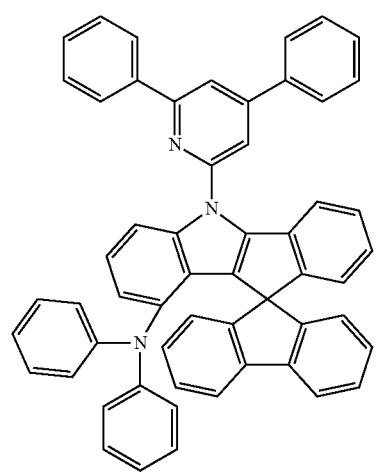
84
-continued
66
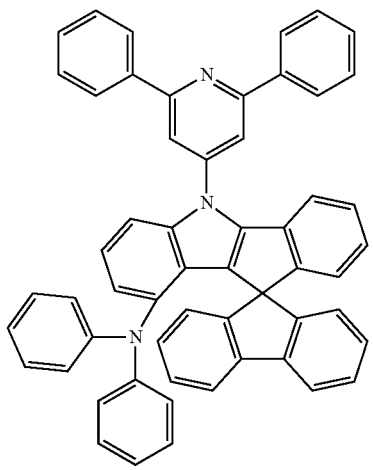
67
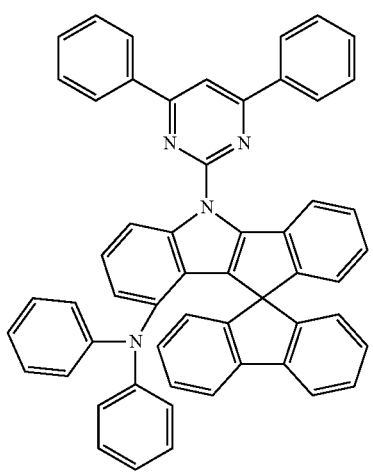
68
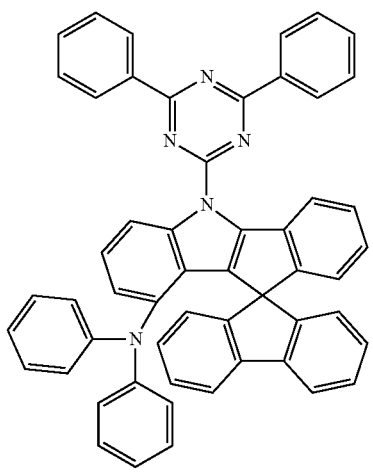

-continued
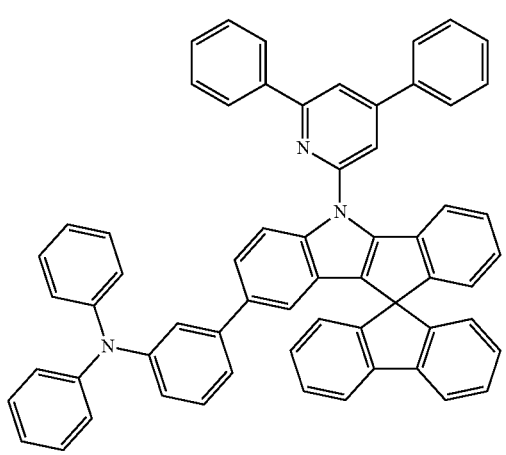
69
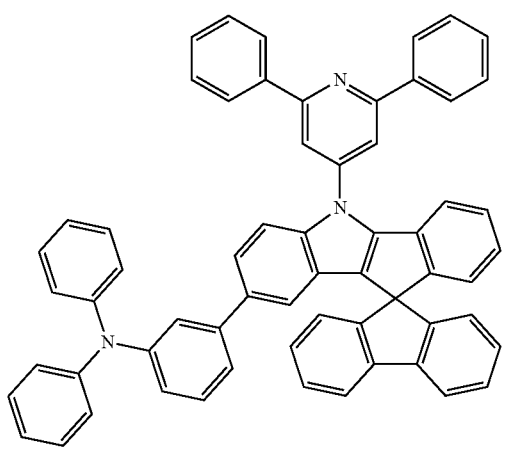
70
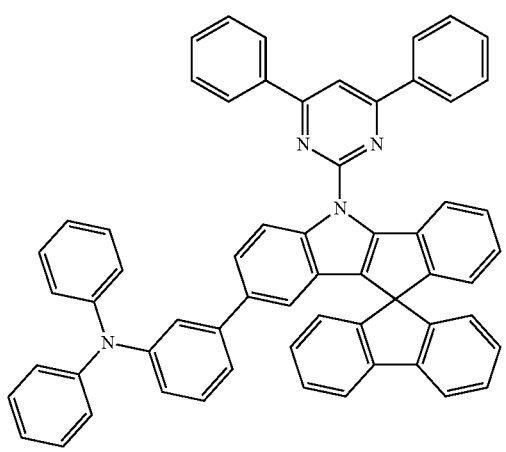
71
-continued
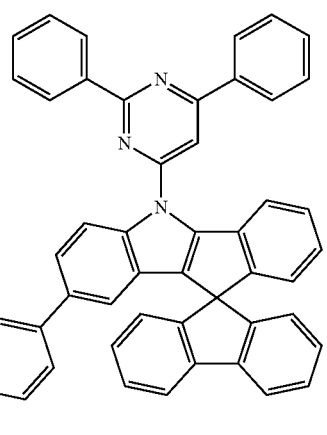
72
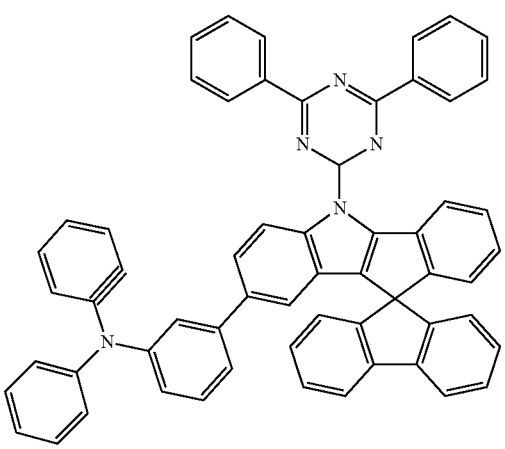
73
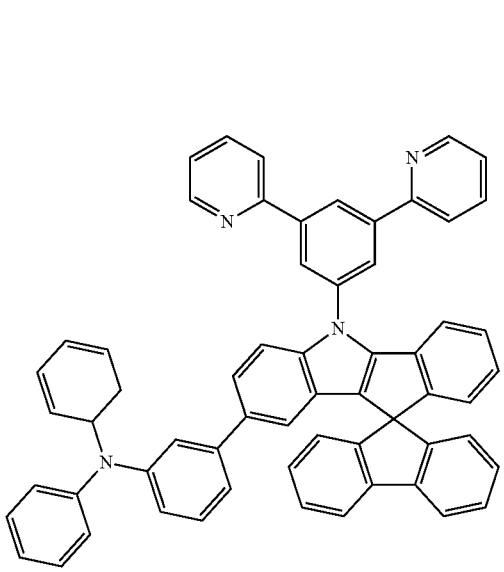
74

75
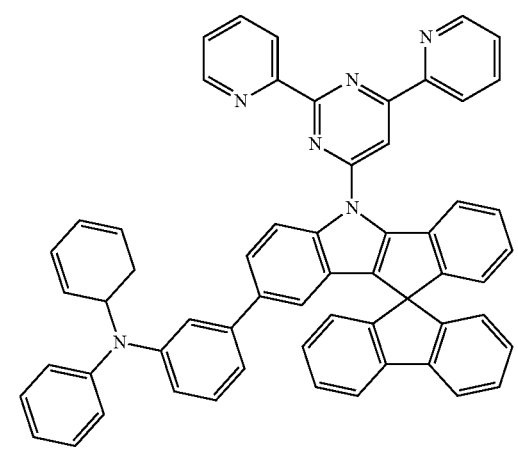
76
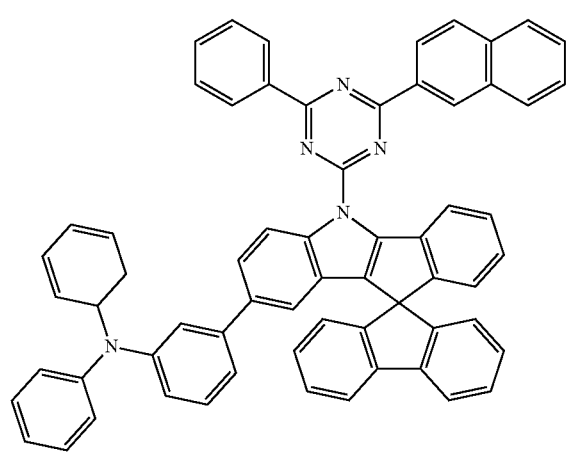
77
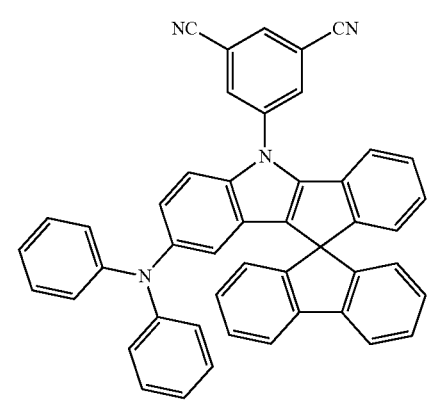
78
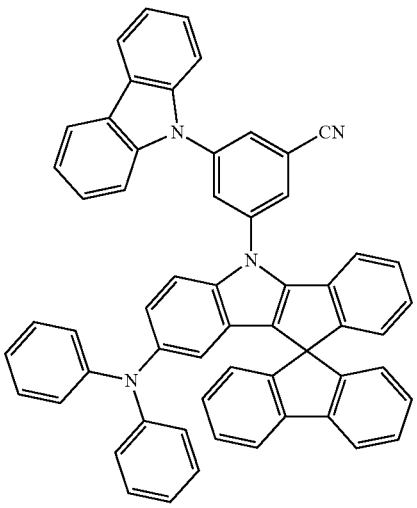
79
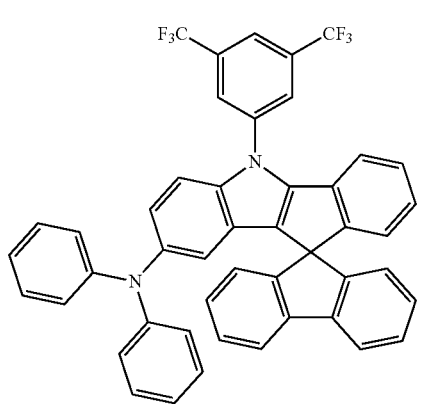
80
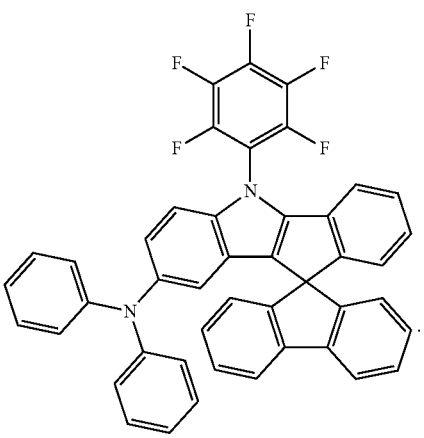
* * * * *